United States Patent
Bickford et al.

(10) Patent No.: US 10,531,805 B2
(45) Date of Patent: Jan. 14, 2020

(54) BIOPHYSICAL SENSING SYSTEMS AND METHODS USING NON-CONTACT ELECTRIC FIELD DETECTORS

(71) Applicant: THE CHARLES STARK DRAPER LABORATORY, INC., Cambridge, MA (US)

(72) Inventors: James A. Bickford, Winchester, MA (US); Louis Kratchman, Quincy, MA (US); Daniel Freeman, Reading, MA (US); Laura Jane Mariano, Somerville, MA (US)

(73) Assignee: THE CHARLES STARK DRAPER LABORATORY, INC., Cambridge, MA (US)

( * ) Notice: Subject to any disclaimer, the term of this patent is extended or adjusted under 35 U.S.C. 154(b) by 95 days.

(21) Appl. No.: 15/720,583

(22) Filed: Sep. 29, 2017

(65) Prior Publication Data

US 2018/0092557 A1    Apr. 5, 2018

Related U.S. Application Data

(60) Provisional application No. 62/482,174, filed on Apr. 5, 2017, provisional application No. 62/402,580, filed on Sep. 30, 2016.

(51) Int. Cl.
*G01R 31/00* (2006.01)
*A61B 5/04* (2006.01)
(Continued)

(52) U.S. Cl.
CPC .............. *A61B 5/04* (2013.01); *A61B 5/0059* (2013.01); *A61B 5/0245* (2013.01);
(Continued)

(58) Field of Classification Search
CPC .... G01R 33/34; G01R 33/36; G01R 33/3804; G01R 33/381; G01R 33/3815;
(Continued)

(56) References Cited

U.S. PATENT DOCUMENTS

| 4,380,735 A | 4/1983 | Bell |
| 4,670,092 A | 6/1987 | Motamedi |

(Continued)

FOREIGN PATENT DOCUMENTS

| CN | 102879655 A | 1/2013 |
| CN | 103390478 A | 11/2013 |

(Continued)

OTHER PUBLICATIONS

Williams et al., "Vacuum Steered-Electron Electric-Field Sensor", Journal of Microelectromechanical Systems, pp. 1-10, Jan. 15, 2013.

(Continued)

*Primary Examiner* — Thang X Le
(74) *Attorney, Agent, or Firm* — Lando & Anastasi, LLP

(57) ABSTRACT

Aspects are generally directed to systems and methods that integrate contactless electric field detectors to measure biophysical signals generated by a body. In one example, a biophysical sensing system includes a sensing assembly including an array of contactless electric field detectors, each of the contactless electric field detectors being configured to sense a corresponding component of an electric field generated by a body, a control system to receive sensor data indicative of the components of the electric field sensed by each of the contactless electric field detectors, the control system being configured to generate an estimate of the electric field based on the sensor data, and a feedback system coupled to at least the control system, the feedback system including at least one feedback interface, the feedback (Continued)

system being configured to operate the feedback interface to provide feedback based on the estimate of the electric field.

22 Claims, 13 Drawing Sheets

(51) Int. Cl.
| | |
|---|---|
| A61B 5/0482 | (2006.01) |
| A61B 5/0478 | (2006.01) |
| A61B 5/053 | (2006.01) |
| A61B 5/00 | (2006.01) |
| A61B 5/0245 | (2006.01) |
| A61B 5/021 | (2006.01) |

(52) U.S. Cl.
CPC .......... *A61B 5/0478* (2013.01); *A61B 5/0482* (2013.01); *A61B 5/0536* (2013.01); *A61B 5/02141* (2013.01); *A61B 2562/0204* (2013.01); *A61B 2562/0247* (2013.01)

(58) Field of Classification Search
CPC ............ G01R 33/385; G01R 33/34007; G01R 33/3635; G01R 33/3642; G01R 33/48; G01R 33/4818; G01R 33/481; G01R 33/4824; G01R 33/446; G01R 33/4835; G01R 33/4828; G01R 33/54; G01R 33/543; G01R 33/561; G01R 33/563; G01R 33/565; G01R 33/5611; G01R 33/5612; G01R 33/583; G01R 33/5659; G01R 33/56518; G01R 33/56536; G01R 33/56572; G01R 33/5614; G01R 33/5616; G01R 33/56509; G01R 33/341; G01R 33/56358; A61B 5/04; A61B 5/0245; A61B 5/0059; A61B 5/0536; A61B 5/0478; A61B 5/0482; A61B 5/02141; A61B 5/055; A61B 5/0555; A61B 5/7278; A61B 5/725; A61B 2562/0247; A61B 2562/0204; A61B 324/30–322

See application file for complete search history.

(56) References Cited

U.S. PATENT DOCUMENTS

| | | | |
|---|---|---|---|
| 5,908,986 A | 6/1999 | Mitamura | |
| 5,945,898 A | 8/1999 | Judy et al. | |
| 6,028,773 A * | 2/2000 | Hundt ................ | G06K 9/0002 174/250 |
| 6,250,156 B1 | 6/2001 | Seshia et al. | |
| 6,429,652 B1 | 8/2002 | Allen et al. | |
| 6,487,864 B1 | 12/2002 | Platt et al. | |
| 6,670,809 B1 | 12/2003 | Edelstein et al. | |
| 6,874,363 B1 | 4/2005 | Foote et al. | |
| 7,185,541 B1 | 3/2007 | Edelstein | |
| 7,231,094 B2 | 6/2007 | Bickford et al. | |
| 7,394,245 B2 | 7/2008 | Brunson et al. | |
| 7,642,692 B1 | 1/2010 | Pulskamp | |
| 7,773,228 B1 * | 8/2010 | Hollingsworth ..... | A61B 5/0059 250/338.1 |
| 7,972,888 B1 | 7/2011 | Li et al. | |
| 8,674,689 B1 | 3/2014 | Nielson et al. | |
| 9,182,454 B1 | 11/2015 | Williams et al. | |
| 2002/0162947 A1 | 11/2002 | Weitekamp et al. | |
| 2003/0140699 A1 | 7/2003 | Pike et al. | |
| 2003/0200807 A1 | 10/2003 | Hulsing | |
| 2004/0187578 A1 | 9/2004 | Malametz et al. | |
| 2005/0234329 A1 * | 10/2005 | Kraus, Jr. .......... | A61B 5/04004 600/409 |
| 2006/0032306 A1 | 2/2006 | Robert | |
| 2007/0096729 A1 | 5/2007 | Brunson et al. | |
| 2010/0099942 A1 * | 4/2010 | Portelli ................ | A61N 1/326 600/13 |
| 2011/0048133 A1 | 3/2011 | Lin et al. | |
| 2011/0054345 A1 * | 3/2011 | Nagatani ................ | A61B 5/05 600/552 |
| 2011/0056294 A1 | 3/2011 | Simoni et al. | |
| 2011/0062820 A1 | 3/2011 | Aoyagi et al. | |
| 2013/0324832 A1 * | 12/2013 | Wu ..................... | A61B 5/04005 600/409 |
| 2014/0023999 A1 * | 1/2014 | Greder ................. | A61B 5/0482 434/236 |
| 2014/0182377 A1 | 7/2014 | Lin et al. | |
| 2014/0308757 A1 | 10/2014 | Ju | |
| 2014/0316188 A1 * | 10/2014 | Peterchev .............. | A61N 2/006 600/14 |
| 2014/0358016 A1 * | 12/2014 | Shapira ................ | A61B 5/0261 600/506 |
| 2015/0226762 A1 | 8/2015 | Seshia et al. | |
| 2016/0023002 A1 | 1/2016 | Schulhauser et al. | |
| 2016/0081577 A1 | 3/2016 | Sridhar et al. | |
| 2016/0116499 A1 | 4/2016 | Thompson | |
| 2016/0120432 A1 * | 5/2016 | Sridhar ................ | A61B 5/6898 600/544 |
| 2016/0341762 A1 | 11/2016 | Waters et al. | |
| 2016/0349283 A1 | 12/2016 | Bramhavar et al. | |
| 2017/0276697 A1 | 9/2017 | Campsie et al. | |
| 2017/0281086 A1 * | 10/2017 | Donaldson ........... | A61B 5/6803 |

FOREIGN PATENT DOCUMENTS

| | | |
|---|---|---|
| CN | 103342562 B | 2/2015 |
| CN | 104459351 A | 3/2015 |
| CN | 106093605 A | 11/2016 |
| DE | 102014204721 A1 | 9/2015 |
| EP | 0702981 A1 | 3/1996 |
| EP | 2199741 A2 | 6/2010 |
| EP | 2466257 A1 | 6/2012 |
| JP | 2011136158 A | 7/2011 |
| WO | 02084315 A1 | 10/2002 |
| WO | 2012071545 A1 | 5/2012 |
| WO | 2014025353 A1 | 2/2014 |
| WO | 2014205356 A2 | 12/2014 |

OTHER PUBLICATIONS

Ando et al., "E-Field Ferroelectric Sensor: Modeling and Simulation", IEEE Instrumentation & Measurement Magazine, pp. 31-37, 2009.

Bai et al., "A novel easy-driving and easy-signal-processing electrostatic field sensor based on piezoresistance and PET lever", Author Submitted Manuscript, pp. 1-15.

Bogue, R., "Plessey launches range of unique electric field sensors", Sensor Review, vol. 32, No. 3, pp. 194-198, 2012.

Chen et al., "Micromachined ac/dc electric field sensor with modulated sensitivity", Sensors and Actuators, No. 245, pp. 76-84, Apr. 26, 2016.

Huang et al., "A novel high-sensitivity electrostatic biased electric field sensor", Journal of Micromechanics and Microengineering, vol. 25, pp. 1-9, Aug. 17, 2015.

Miles et al., "Report on Non-Contact DC Electric Field Sensors", Jun. 23, 2009.

Datskos et al., "Using Micro-Electro-Mechanical Systems (MEMS) as Small Antennas", IEEE, 2012.

Toney et al., "Detection of Energized Structures with an Electro-Optic Electric Field Sensor", IEEE, pp. 1364-1369, May 2014.

Angelakis et al., "EEG Neurofeedback: A Brief Overview and an Example of Peak Alpha Frequency Training for Cognitive Enhancement in the Elderly", The Clinical Neuropsychologist, vol. 21, pp. 110-129, Feb. 16, 2007.

Ashrafulla, S., "EEG and MEG: functional brain imaging with high temporal resolution", Jun. 2013, <URL: https://ngp.usc.edu/files/2013/06/Syed_EEG_MEG.pdf>.

Basar et al., "A review of brain oscillations in cognitive disorders and the role of neurotransmitters", Brain Research, vol. 1235, pp. 172-193, Jul. 2, 2008.

(56) References Cited

OTHER PUBLICATIONS

Choi, K., "Electroencephalography (EEG) based neurofeedback training for brain-computer interface (BCI)", pp. 1-26, Sep. 2013.
Gabrielson, T.B., "Mechanical-Thermal Noise in Micromachined Acoustic and Vibration Sensors", IEEE Transactions on Electron Devices, vol. 40, No. 5, pp. 903-909, May 1993.
Grummett et al., "Measurement of neural signals from inexpensive, wireless and dry EEG systems", Physiological Measurement, vol. 36, pp. 1469-1484, 2015.
Heintzelman et al., "Characterization and Analysis of Electric-field Sensors", IEEE, Dec. 17, 2015.
Kingsley et al., "Photrodes for physiological sensing", SPIE 5317, Optical Fibers and Sensors for Medical Applications IV, Jun. 2004.
Niv, S., "Clinical efficacy and potential mechanisms of neurofeedback", Personality and Individual Differences, vol. 54, pp. 676-686, Jan. 24, 2013.
Othmer, S., "Neuromodulation technologies: An attempt at classification", Introduction to Quantitative EEG and Neurofeedback: Advanced Theory and Applications, second edition, pp. 1-27, 2009.
Prance, H., "Sensor Developments for Electrophysiological Monitoring in Healthcare", Applied Biomedical Engineering, pp. 265-286, Aug. 2011.
Schalk et al., "Brain Sensors and Signals", A Practical Guide to Brain-Computer Interfacing with General-Purpose Software for Brain-Computer Interface Research, Data Acquisition, Stimulus Presentation, and Brain Monitoring, pp. 9-35, 2010.
Stikic et al., "Modeling temporal sequences of cognitive state changes based on a combination of EEG-engagement, EEG-workload, and heart rate metrics", Frontiers in Neuroscience, vol. 8, article 342, pp. 1-14, Nov. 2014.
Bickford, J. "Monitoring Brain Activity (E-Field Sensor)", Draper, accessed Oct. 31, 2016.
Budzynski et al., "Introduction to Quantitative EEG and Neurofeedback: Advanced Theory and Applications," 2nd ed., Elsevier (2009), chapters 1, 6, 8 and 16.
Kelly et al., "Progress Toward Forecasting of Space Weather Effects on UHF Satcom after Operation Anaconda", Space Weather, Sep. 12, 2014, doi: 10.1002/2014SW001081.
Bernstein et al., "Low-Noise MEMS Vibration Sensor for Geophysical Applications," Journal of Microelectromechanical Systems, val. 8, No. 4, pp. 433-438, 2009.
Dilella et al., "A Micromachined Magnetic-Field Sensor Based on an Electron Tunneling Displacement Transducer," Sensors and Actuators. vol. 86, pp. 8-20, 2000.
Dong et al., "Push-Pull Mode Magnetostrictive/Piezoelectric Laminate Composite with an Enhanced Magnetoelectric Voltage Coefficient," Applied Physics Letters, vol. 87, pp. 62502. 2005.
Kyynarainen et al., "A 3D Micromechanical Compass," Sensors and Actuators A, vol. 142, pp. 561-568. 2008.
Latorre et al., "Micromachined CMOS Magnetic Field Sensor with Ferromagnetic Actuation," Proceedings of SPIE, vol. 4019, 2000.
Tatarchuk et al., "A MEMS DC Current Sensor Utilizing Neodymium Rare Earth Magnets," Additional Conferences (Device Packaging, HiTEC, HiTEN, & CICMT): Jan. 2014, vol. 2014, No. DPC, pp. 001046-001071.
Vasquez et al., "Optically-Interrogated Zero-Power MEMS Magnetometer", Journal of Microelectromechanical Systems, vol. 16, No. 2, pp. 336-343, Apr. 2007.
Wickenden et al., "Polysilicon Xylophone Bar Magnetometers," SPIE vol. 3876, pp. 267-273. Sep. 1999.
Yang et al., "Ferromagnetic Micromechanical Magnetometer," Sensors and Actuators A, vol. 97-98, pp. 88-97, 2002.
Zhao et al., "Fabrication and Characterization of All-Thin-Film Magnetoelectric Sensors," Applied Physics Letters, vol. 94, p. 243507. 2009.
Chen et al. "MEM Electric Field Sensor using Force Deflection with Capacitance Interrogation", Power & Energy Society General Meeting. IEEE (2013).
Kuriyama et al. "Electrostatic Field Distribution Measurement Using Silicon Micro-mirror Array", IEEE International Symposium on Electromagnetic Compatibility (2012), pp. 351-356.
Goel, M. "Electret sensors, filters and MEMS devices: New challenges in materials research", Current Science (2003) vol. 85, No. 4, pp. 443-453.
International Search Report and Written Opinion for application No. PCT/US2017/054461 dated Jan. 18, 2018.
Denison et al., "A Self-Resonant MEMS-Based Electrometer", IEEE Instrumentation and Measurement Technology Conference Proceedings, pp. 1-5, 2007.
Petrov et al., "Electric Field Encephalography as a Tool for Functional Brain Research: A Modeling Study", PLOS ONE, vol. 8, No. 7, Jul. 3, 2013.

* cited by examiner

BIOPHYSICAL SENSING SYSTEMS AND METHODS USING NON-CONTACT ELECTRIC FIELD DETECTORS

CROSS REFERENCE TO RELATED APPLICATIONS

This application claims priority under 35 U.S.C. § 119(e) to U.S. Provisional Application Ser. No. 62/402,580, titled "INTEGRATION OF NON-CONTACT ELECTRIC FIELD SENSOR FOR BIOPHYSICAL APPLICATIONS," filed on Sep. 30, 2016, and to U.S. Provisional Application Ser. No. 62/482,174, titled "INTEGRATION OF NON-CONTACT ELECTROMAGNETIC SENSORS FOR BIOPHYSICAL APPLICATIONS," filed on Apr. 5, 2017, each of which are hereby incorporated herein by reference in their entirety.

BACKGROUND

The human body generates static and time-varying electromagnetic fields which may be measured and used in numerous applications. However, these fields are often faint, even in close proximity to the body, and attenuate as the distance from the human body is increased. For example, ionic currents within neurons of the brain will generate voltage fluctuations and magnetic fields during synaptic transmission. While these fields have proved challenging to accurately measure, some approaches exist for directly detecting the electrical activity produced by the body. Typically, numerous electrodes are arranged to measure voltages at a patient's scalp with electroencephalography (EEG), or highly sensitive magnetometers are employed during magnetoencephalography (MEG) to detect magnetic fields. Other techniques, such as functional magnetic resonance imaging (f-MRI), are able to indirectly measure electrical activity via blood flow to relevant regions of the brain.

SUMMARY

Aspects and examples described herein are generally directed to systems and methods that integrate contactless electric field detectors to measure biophysical signals generated by the body, such as time-varying electromagnetic fields generated by the brain. Based on collected sensor data, particular examples of the systems described herein may control one or more feedback systems to assess, diagnose, enhance, manipulate, or otherwise address a subject's mental state or physical state. As further described herein, various aspects and examples provide a low-cost, low-noise, and non-invasive microelectromechanical system (MEMS) electric field detector array, and associated sensing system, that may be operated with a feedback system to provide advancements in education and training, human-machine interfaces, medical diagnostics, and treatment of medical disorders. Specifically, some examples of the array of contactless electric field detectors permit the use of electric field encephalography (EFEG) to directly measure electrical activity of the brain, muscles, nerves, and other regions of the body. Examples of the array of contactless electric field detectors also permit the use of high precision electric field tomography to generate an image of a body or object.

According to an aspect, provided is a biophysical sensing system. In one example, the biophysical sensing system comprises a sensing assembly including an array of contactless electric field detectors, each of the contactless electric field detectors being configured to sense a corresponding component of an electric field generated by a body of a subject, a control system coupled to the sensing assembly to receive sensor data indicative of the components of the electric field sensed by each of the contactless electric field detectors, the control system being configured to generate an estimate of the electric field based at least in part on the sensor data, and a feedback system coupled to at least the control system, the feedback system including at least one feedback interface, the feedback system being configured to operate the feedback interface to provide feedback to the subject based on the estimate of the electric field. According to various examples, the component of the electric field is a vector component. In various other examples, the component of the electric field is a scalar magnitude or a scalar direction.

According to various examples, the feedback interface is at least one of a visual display, a speaker, a haptic transducer, a heating or cooling source, and a chemical source. In some examples, the feedback system includes a housing configured to attach to the subject, the at least one of the visual display, the speaker, the haptic transducer, the heating or cooling source, and the chemical source being coupled to the housing. According to various examples, the feedback is at least one of a series of visual images from the visual display, an auditory feedback from the speaker, a vibration or pressure sensation from the haptic transducer, a heat stimuli or a cooling stimuli from the heating or cooling source, and a chemical stimulus from the chemical source. In certain examples, the control system is configured to compare the estimate of the electric field to an electric field template of a mental state, and instruct the feedback system to operate the feedback interface to induce a neural response in the subject based on a difference between the estimate of the electric field and the electric field template of the mental state.

In various examples, the neural response includes one or more neural oscillations, the feedback system being configured operate the feedback interface to suppress or augment the one or more neural oscillations. In certain other examples, the neural response includes an evoked potential, the feedback system being configured operate the feedback interface to modify the evoked potential.

According to various examples, the control system is configured to compare the estimate of the electric field to an electric field template of a mental state, and the feedback system is configured to operate feedback interface to match a subsequent estimate of the electric field to the electric field template of the mental state. In certain examples, the feedback interface includes at least one active stimulator, the feedback system being configured to operate the active stimulator to provide a stimulus to the subject based at least in part on the estimate of the electric field. In various examples, the control system is further configured to generate an input for a human-machine interface based at least in part on the estimate of the electric field. In at least a few examples, each of the contactless electric field detectors of the array of contactless electric field detectors is a microelectromechanical system (MEMS) electric field detector including at least a proof mass, and where each of the contactless electric field detectors is configured to sense the corresponding component of the electric field based on a displacement of the proof mass.

According to various examples, the feedback interface is active stimulation from a magnetic and/or electric source located in proximity to the body. In some examples, interface is the modification of the environment, tasking and/or other type of input provided to the test subject. In certain examples, the feedback is provided to external users or machines which may directly or indirectly interact with the primary test subject. In various examples, the housing is a wrap that surrounds all or part of the body.

According to another aspect, provided is a biophysical sensing assembly. In at least one example, the biophysical sensing assembly comprises an array of contactless electric field detectors, each of the contactless electric field detectors being configured to sense a corresponding component of an electric field generated by a body of a subject, control electronics electrically coupled to each of the contactless electric field detectors, the control electronics configured to provide sensor data based on the corresponding components of the electric field, an electromagnetic shield interposed between the array of contactless electric field detectors and the control electronics, the electromagnetic shield being positioned to electromagnetically isolate at least the array of contactless electric field detectors from electromagnetic interference from the control electronics, and a housing positioned to enclose at least the array of contactless electric field detectors, the control electronics, and the electromagnetic shield, and to suspend the array of contactless electric field detectors relative to the subject.

According to various examples, the housing is a headpiece. In other examples, the housing is a wrap. In some examples, the electromagnetic shield is a Faraday cage. According to some examples, the control electronics include at least one auxiliary sensor positioned proximate at least one contactless electric field detector of the array of contactless electric field detectors to detect a source of noise in the sensor data. In at least a few examples, the auxiliary sensor includes at least one of an additional electric field detector positioned to sense an external electric field, an inertial sensor positioned to sense movement of the subject, and a physiological sensor to sense a physiological characteristic of the subject. In various examples, each of the contactless electric field detectors of the array of contactless electric field detectors is a microelectromechanical system (MEMS) electric field detector including at least a proof mass, and where each of the contactless electric field detectors is configured to sense the corresponding component of the electric field based on a displacement of the proof mass.

According to another aspect, provided is a biophysical feedback method. In one example, the biophysical feedback method comprises sensing components of an electric field generated by a body of a subject at each of an array of contactless electric field detectors positioned proximate the subject, receiving sensor data from the array of contactless electric field detectors at a control system, the sensor data indicative of the components of the electric field sensed by each of the contactless electric field detectors of the array of contactless electric field detectors, generating, at the control system, an estimate of the electric field based at least in part on the sensor data, and operating at least one feedback interface of a feedback system to provide feedback to the subject based on the estimate of the electric field.

In various examples, the biophysical feedback method further comprises comparing the estimate of the electric field to an electric field template of a mental state, and controlling the feedback interface to match a subsequent estimate of the electric field to the electric field template of the mental state. In some examples, the bio physical method further comprises comparing the estimate of the electric field to an electric field template of a mental state, and controlling the feedback interface to induce a neural response in the subject based on a difference between the estimate of the electric field and the electric field template of the mental state.

According to some examples, the neural response includes one or more neural oscillations, and operating the at least one feedback interface includes at least one of displaying a series of visual images on a visual display, radiating auditory feedback from a speaker, generating a vibration or pressure sensation from a haptic transducer, generating a heat stimuli or a cooling stimuli from a heating or cooling source, and providing a chemical stimulus from a chemical source, to suppress or augment the one or more neural oscillations. In various examples, the neural response includes an evoked potential, and operating the at least one feedback interface includes displaying a series of visual images on a visual display, radiating auditory feedback from a speaker, generating a vibration or pressure sensation from a haptic transducer, generating a heat stimuli or a cooling stimuli from a heating or cooling source, and providing a chemical stimulus from a chemical source, to modify the evoked potential. According to various examples, sensing the components of the electric field at each of the array of contactless electric field detectors includes detecting the components based on a displacement of a corresponding proof mass of each of the contactless electric field detectors. In some examples, the method further comprises generating an input for a human-machine interface based at least in part on the estimate of the electric field.

According to an aspect, provided is an electric field tomography (EFT) system. In one example, the EFT system comprises a plurality of electrodes including at least a first electrode and a second electrode positioned to provide an electric field to an object positioned between the first electrode and the second electrode, an array of contactless electric field detectors, each of the contactless electric field detectors being configured to sense a distortion of the electric field from the object and provide sensor data based at least in part on the sensed distortion, where each of the contactless electric field detectors of the array of contactless electric field detectors is a microelectromechanical systems (MEMS) electric field detector, and a control system coupled to the array of contactless electric field detectors to generate an image of the object based on the sensor data. In various examples, each of the contactless electric field detectors includes a proof mass and is configured to sense the distortion of the electric field based on a displacement of the proof mass.

Various examples are directed to a biophysical sensing system configured to detect electric field component. In some examples, the system includes integrated inertial sensors, eye trackers, physiological sensors (e.g., pulse, muscle contraction), cameras, magnetometers, and/or other related sensors to compensate for vibration, body motion, and other error sources. In some examples, the system includes a communication interface (wired or wireless) that routes measured sensor data from an array of electric field detectors to a digital signal processor. In further examples, the digital signal processor may include one or more algorithms that utilize auxiliary sensor data to remove errors in the sensor data and produce an optimal estimate of the electric field components.

According to various examples, the biophysical sensing system is configured to reconstruct a spatial distribution and temporal changes in activity of a brain based on the electric field sensor data. The system may include a control law to generate a feedback signal for a feedback system that may drive a subject behavior towards a desired response. In some particular examples, the system includes adaptive control laws that adjust subject behavior and performance over time. In some examples, the system includes a feedback system to provide behavioral feedback based on one or more control signal generated by the control law, where the feedback system may or may not be mechanically integrated within a housing of the system. In some examples, the behavioral feedback includes external stimuli from television monitors, speakers, heat or cooling sources, and/or other sources. In other examples, the behavioral feedback includes stimuli from body mounted interfaces such as a VR/AR helmet, headphones, a haptic transducer, a trans-cranial stimulator, and/or other interfaces.

According to an aspect, provided is a sensor array formed from one or more contactless electric field detectors. The sensor array may be positioned within a small volume that is electrically shielded from auxiliary sensors, electronics, and environmental influences. In some examples, the contactless electric field detectors are positioned external to a body of a subject and not in direct-contact with the body. In some examples, the contactless electric field detectors are mounted to a hospital bed, couch, chair, wall, or other room furnishing. In at least one example, the contactless electric field detectors are positioned to measure electrical activity of the subject's heart.

According to another aspect, provided is biophysical sensing system that includes an array of contactless electric field detectors that provide an input to a control loop with one or more feedback interfaces. In one example, a feedback interface is a behavioral interface. In one example, the feedback interface is configured to modify tasking based on measured brain activity, such as evoked potentials or other electrical processes in the brain, in addition to other physiological measurements. In other examples, the feedback interfaces is a passive behavioral feedback mechanism that provides visual, auditory, olfactory, and/or haptic feedback to enhance selected neural oscillations or other desired brain behavior. In still other examples, the feedback interface is an active behavioral feedback mechanism. The active behavioral feedback mechanism may provide behavioral feedback based on active stimuli (e.g., transcranial magnetic stimulation (TMS) or transcranial direct-current stimulation (TDS)) to enhance selected neural oscillations or other desired brain behavior. In other examples, the feedback interface is an indirect behavioral feedback mechanism that provides output to external users or machines. The output may include information to enable a diagnostic medical test to be performed on a subject.

In other examples, the biophysical sensing system may be applied towards education and training using neurofeedback techniques. In certain examples, the array of contactless electric field detectors and control system provide input to a control law that modifies the output of a feedback interface to drive a subject response towards a desired outcome. The desired outcome may enhance an educational process, skill acquisition, or behavior that is learned consciously or subconsciously. In some examples, the sensing system implements a control law to operate the feedback interfaces to modify brain behavior based on a pre-determined template. In some examples, the feedback interfaces may provide behavioral feedback to align a mental state of the subject with a known neural correlate, or other pattern associated with improved neural performance. In some examples, the sensing system may be applied to enhanced learning in areas such as music, math, reading, writing, comprehension, memorization, attention, concentration and other areas where enhancement of a skill is required.

In various examples, a biophysical sensing system that includes an array of contactless electric field detectors and a feedback system, as discussed herein, may have utility in a variety of applications. In various examples, the sensing system may be applied to direct emotional enhancement to relieve depression, pain, and related conditions. Specifically, the sensing system may train the brain to avoid undesirable neural patterns and enhance desirable neural patterns. In other examples, the sensing system may be applied to general cognitive enhancement, or to avoid a cognitive decline associated with age or other neurological conditions. In some examples, the sensing system may be applied to traditional educational settings such as grammar schools, secondary schools, and post-secondary educational settings. According to certain examples, the sensing system may be applied to home based training of children and adults. In some examples the sensing system may be applied to professional training and skill enhancement in the workplace (civilian or government). In still other examples, the sensing system may be applied to patients in a clinical environment such as a hospital or nursing home.

According to various aspects, provided is an electric field tomography (EFT) system that includes one or more contactless electric field detectors. In various examples, the contactless electric field detectors may be arranged in an array. The array of contactless electric field detectors may be oriented to measure projections of an electric field of a subject's body in two or more independent directions. Some examples of the EFT system may include a power source to control an electric field between two electrodes that provide the electric field. In some examples, the electrodes are attached to a motor that can rotate the electrodes. In a particular example, the electrodes are attached to a motor than causes the electrodes to collectively translate. In some examples, the electrodes are attached to one or more robots, which can arbitrarily position and orient the electrodes. In various examples the EFT system includes a control system to modulate the power source, and thus modify the electric field generated between the electrodes. In some examples, the control system is configured to reconstruct an image of an object (e.g., a subject) placed near the electrodes by processing sensor data received from the array of contactless electric field detectors. Some examples include an electric shield (e.g., a Faraday cage) to enclose at least the array of contactless electric field detectors. Some examples may include multiple electric shields.

According to various aspects, provided is an electric field encephalography (EFEG) system that includes one or more contactless electric field detectors arranged in an array. In certain examples, the EFEG system may be applied towards the diagnosis and treatment of conditions such as ADHD, autism, dyslexia, epilepsy, traumatic brain injury, affective disorders, addiction, sleep disorders, obsessive-compulsive disorder, pain, CTE, PTSD, and Alzheimer's disease, among other forms of dementia or brain disease. In some examples, the EFEG system quantifies the severity and extent of the neurological condition. In certain examples, the EFEG system selects a treatment option based on the measured brain behavior. The selected treatment options may include treatment based on applying neuro-feedback to reduce symptoms of the diagnosed condition.

According to various other examples, the EFEG system may be applied towards rapid and non-invasive cognitive assessment of a subject relative to a baseline from a group or a prior state. In certain examples, the EFEG system is configured for use during sporting events for the detection of concussions. The EFEG system may perform measurements after a collision, or may continuously monitor a player as part of the equipment (e.g., a helmet) worn by that player. In certain other examples, the EFEG system is configured for use by emergency responders, medical professionals, or professionals in a military environment to detect neurological injuries after a collision, explosion, or other traumatic event. In particular examples, the EFEG system is configured to measure cognitive performance in a medical application to quantify a condition or treatment progress.

In various examples, the EFEG system may be applied to provide a post-event insurance claim assessment to confirm or quantify the extent of a given injury or condition. In other examples, the EFEG system may be applied to rank individuals in educational and professional settings including an assessment of a retention rate of relevant information and an individual's cognitive capabilities. In other examples, the EFEG system may be applied to assess neurological function following symptoms of stroke. In still other examples, the EFEG system may be applied to diagnose and monitor coma patients.

As discussed, the EFEG system may have a variety of applications in a variety of fields. In various examples, the EFEG system may be applied to determine the occurrence of a brain death as a step in an organ donation procedure. In other examples, the EFEG system may be applied to diagnose and/or monitor locked-in syndrome, or detect brain tumors.

According to another aspect, provided is an array of contactless electric field detectors and corresponding control system that provides input to a brain-machine interface. In some examples, sensor data from the contactless electric field detectors may be used to further understand unspoken intent. In some examples, the array of contactless electric field detectors may enhance symbiotic human and machine processing (e.g., enhanced processing with P300 evoked potential activation following object or event recognition). In various examples, the control system may provide an input for electronic games and entertainment. In other examples, the control system and array of contactless electric field detectors may transcribe thoughts for human to human communication via an intermediate link. In other examples, the control system may be applied to enhance speech recognition and communication. In some examples, the control system and array of contactless electric field detectors may be applied in robotic interfaces and neuro-prostheses. In some examples, the control system and array of contactless electric field detectors may be applied to provide a general input and/or control signal for a computer, other electrical device, or machinery.

In certain examples, the control system and array of contactless electric field detectors may be applied to monitor operators of machinery, heavy equipment, vehicles, aircraft, ships, power plants, and other industrial applications to enhance safety (e.g., detect inattention) and improve job performance. In other examples, the control system and array of contactless electric field detectors may be applied to determine an optimum time to present information to a user and/or a preferred format for such information. In other examples, the control system and array of contactless electric field detectors may be applied to determine whether presented information was properly recognized and processed by an audience, and whether it needs to be repeated.

In other examples, the control system and array of contactless electric field detectors may be applied to control vehicles, including automobiles, aircraft, nautical vessels, heavy industrial vehicles (e.g., trucks, excavators, cranes, agricultural vehicles, mining vehicles, forestry vehicles, and waste hauling and removal vehicles), military vehicles, powered wheelchairs, personal mobility devices, and recreational vehicles. In particular, the control system and array of contactless electric field detectors may be applied to detect fatigue or inattention, provide input for vehicle or accessory control, and/or detect neurological responses to obstacles or other hazardous travel conditions. In other examples, the control system and array of contactless electric field detectors may be applied to detect lies and mal-intent. In particular, the array of contactless electric field detectors may measure knowledge of a given event, person, place, or other fact. In various examples, the control system may measure a veracity of a statement or response based on sensor data from the array of detectors. In other examples, the control system and array of contactless electric field detectors may correlate an EFEG response against baseline responses of an individual or a larger group. In specific examples the control system may analyze lie detection and mal-intent data with other bio-physical data for enhanced performance.

In other examples, the control system and array of contactless electric field detectors may be applied to advertising and related applications including political polling. In particular examples, the array of contactless electric field detectors may detect an interest level and a response to a given advertisement. Based on the sensor data, the control system may determine an optimal time to deliver a given input. In some examples, the control system and array of contactless electric field detectors may be applied to measure a response to an event, person, situation or other scenario to estimate a state of an individual or a larger group.

Other aspects provide a control system and array of contactless electric field detectors configured to measure nerve potential, muscle contractions, and other electrical behavior of a subject's body. In some examples, the control system and array of contactless electric field detectors may be applied to robotic interfaces and neuro-prostheses. In other examples, the array of contactless electric field detectors may sense vagus nerve stimulation for the treatment of epilepsy, depression, inflammation, and other medical conditions. In other examples, the control system and array of contactless electric field detectors may measure heart rate, heart rhythm, and/or other cardiac electrical behavior. In still other examples, the control system and array of contactless electric field detectors may be applied to bedside heart monitors.

According to another aspect, provided is a surgical instrument navigation system. In various examples, the surgical instrument navigation system includes an electrically conductive surgical instrument coupled to an electrical power source. The surgical instrument navigation system may include an electrode that is electrically connected to a terminal of the power source, the terminal that the electrode is coupled to having an opposite polarity of a terminal that the surgical instrument is coupled to. In some examples, the surgical instrument navigation system includes a conductive shield that fully encloses the other components of the surgical instrument navigation system. In various examples, the surgical instrument navigation system includes an array of contactless electric field detectors arranged between the surgical instrument and a grounded enclosure.

In various examples, the surgical instrument navigation system includes an array of contactless electric field detectors oriented to measure a projection of an electric field produced by the electrode, in two or more independent directions. In some examples, the surgical instrument tracking system includes a control system coupled to the array of detectors to record the output of each contactless electric field detector. In various examples, the control system may calculate a position of the surgical instrument based on sensor data from the array of contactless electric field detectors. In particular, the control system may calculate an orientation of surgical instrument from the sensor data.

According to another aspect, provided is a control system and an array of contactless electric field detectors for measurement of muscle activity. In some examples, the array of contactless electric field detectors may measure muscular activity and provide an input to a powered prosthesis control system. In particular examples, the array of contactless electric field detectors may be implantable. In some examples, the array of contactless electric field detectors may measure muscular activity and provide an input to a powered exoskeleton. In some examples, the array of contactless electric field detectors may measure muscular activity and provide an input to a machine control system.

In various examples, the control system and the array of contactless electric field detectors may monitor muscular activity during physical rehabilitation. Particular measurements may include measurements of lower body muscular activity to aid in rehabilitation of spinal cord injuries. In various examples, the control system and the array of contactless electric field detectors may be applied to stress monitor muscular tension. In other examples, the control system and the array of contactless electric field detectors may be applied to diagnose muscular disorders, such as inflammatory myopathies, polymyositis, dermatomyositis, inclusion body myopathy, and muscular dystrophies. In other examples, the control system and the array of contactless electric field detectors may be applied to monitor eyelid muscular activity to detect rapid eye movements corresponding to the rapid eye movement stage of mammalian sleep. In some examples, the control system and the array of contactless electric field detectors may be applied to detect contraction of the throat muscles for use in treatment of dysphagia. In some examples, the control system and the array of contactless electric field detectors may be applied to monitor muscle tremors. In various examples, the control system may generate control signals for a feedback system to provide audio, visual, or tactile feedback derived from the measured muscular activity.

According to another aspect, provided is a control system and array of contactless electric field detectors for various other medical applications. In one example, the control system and the array of contactless electric field detectors may be applied to monitor the safety and efficacy of general anesthesia. In further examples, the control system and the array of contactless electric field detectors may monitor a depth of anesthesia, in complement to, or as a replacement for, electroencephalographic monitoring. In another example, the control system and the array of contactless electric field detectors may detect locked-in syndrome and failures of anesthesia. In still other examples, the control system and the array of contactless electric field detectors may provide a replacement for electromyographic electrodes in neuromuscular monitoring devices.

In one example, the control system and the array of contactless electric field detectors may be incorporated within swallowable medical devices to diagnose gastrointestinal disorders. In one example, the control system and the array of contactless electric field detectors may measure contractions of stomach muscles, measure peristaltic contractions of intestines, or detect polyps, ulcers, or other abnormalities of the gastrointestinal tract.

Other aspects of the present disclosure provide an array of contactless electric field detectors that enhances various existing electronic systems and imaging capabilities. For instance, the array of contactless electric field detectors may be incorporated within an EFEG system that is integrated with MEG, MRI, PET, or other bio-physical sensors to generate composite medical imaging data. The composite medical imaging data can be used for enhanced diagnosis and/or treatment quality.

In some examples, the EFEG system may measure evoked potentials in a subject without the need for averaging each measurement, due to its lower relative noise. In some examples, the EFEG system may be applied to discover new brain functions and behavior. The EFEG system may measure evoked potentials (e.g. P-300), neural oscillations (alpha waves), and other brain behavior as an input for neurofeedback loops. Feedback can be passively provided in the form of visual, auditory, and/or haptic modalities from a feedback system.

Still other aspects, examples, and advantages are discussed in detail below. Embodiments disclosed herein may be combined with other embodiments in any manner consistent with at least one of the principles disclosed herein, and references to "an embodiment," "some embodiments," "an alternate embodiment," "various embodiments," "one embodiment" or the like are not necessarily mutually exclusive and are intended to indicate that a particular feature, structure, or characteristic described may be included in at least one embodiment. The appearances of such terms herein are not necessarily all referring to the same embodiment. Various aspects and embodiments described herein may include means for performing any of the described methods or functions.

BRIEF DESCRIPTION OF THE DRAWINGS

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the disclosure. In the figures, each identical or nearly identical component that is illustrated in various figures is represented by a like numeral. For purposes of clarity, not every component may be labeled in every figure. In the figures.

DETAILED DESCRIPTION

Figure 1:
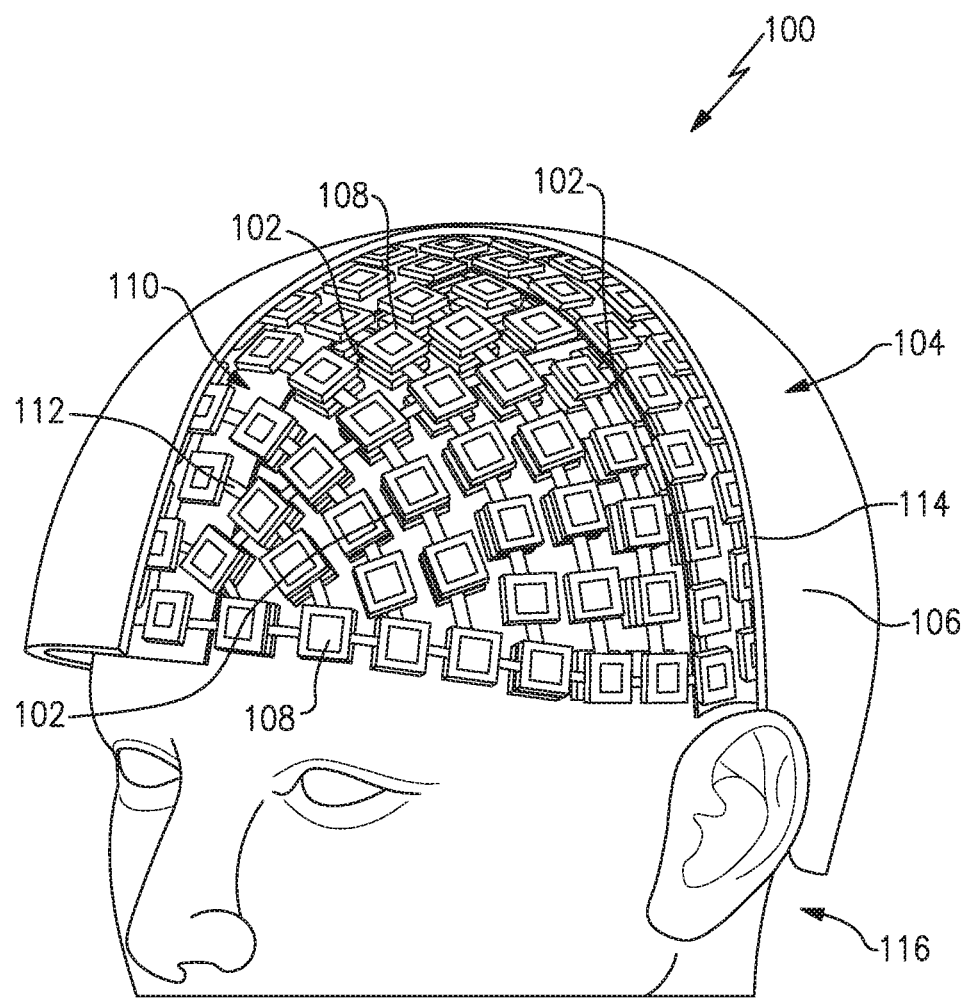
FIG. 1 is a biophysical sensing assembly according to various examples described herein.

Aspects and examples described herein are generally directed to biophysical sensing systems and methods that integrate an array of contactless electric field detectors to measure biophysical signals generated by the body. In various examples, the array of contactless electric field detectors permits the use of electric field encephalography (EFEG) to directly measure time-varying electromagnetic fields generated by the body, and in particular, the brain. Based on the array of sensed data, a spatial distribution and the temporal activity of the electric field may be monitored.

Certain examples of the systems described herein include a feedback system which may be controlled to provide visual, auditory, chemical, temperature, and/or haptic feedback to a subject to assess, diagnose, enhance, manipulate, or otherwise address a subject's mental state or physical state. As further described herein, various aspects and examples of the biophysical sensing system, and associated array of contactless electric field detectors, provide advancements in education and training, human-machine interfaces, medical diagnostics, and treatment of medical disorders.

As discussed above, the human body generates static and time-varying electromagnetic fields which are often difficult to resolve. While some techniques for measuring these electromagnetic fields currently exist, these techniques are typically expensive, time-consuming, physically invasive, or unreliable. Electroencephalography (EEG) typically requires numerous electrodes placed on the scalp of a subject. Electroencephalography can provide complimentary information to traditional magnetoencephalography (MEG) processes as each EEG electrode responds to a different orientation of dipole current sources in the brain. For instance, EEG electrodes may be more sensitive to neocortical dipole sources in the gyri regions of the brain. EEG systems may also be more useful than MEG systems when magnetic shielding is not practical.

However, typical electroencephalographs utilize gel-based wet electrodes. Each electrode is painstakingly applied and properly arranged on the scalp of a subject. This application process is time-consuming and uncomfortable for most subjects. Moreover, subject hair, air pockets, and unintentional movement of the electrodes can each introduce errors into the sensed measurements. While dry electrodes and capacitive sensors can reduce some of these logistical issues, dry electrodes and capacitive sensors often suffer from noise artifacts due to electrical impedance changes associated with movement, sweating, and environmental factors. Medical imaging technology such as functional magnetic resonance imaging (f-MRI), computerized tomography, and positron emission tomography (PET) may resolve some of these issues, but often does so at the expense of an increased cost and an increased spatial footprint. Moreover, these systems often offer a limited response rate, as brain activity is indirectly measured.

Accordingly, in addition to offering functionality that is not currently made available by most typical biophysical sensing and imaging systems, examples of the biophysical signal sensing systems and methods described herein incorporate an array of non-invasive, low-noise compact, electric field detectors. For instance, each electric field detector may achieve a low-noise performance, such as less than 1 mV/m/rtHz at 10 Hz performance, at a size much smaller than typical EEG electrodes (e.g., a size less than 1 cm$^3$). Moreover, as a result of the accuracy and response of the array of electric field detectors, various examples of the biophysical sensing systems described herein may include, or be integrated within, a feedback system that enhances education and training (e.g., for children and/or adults), improves the accuracy and response of human-computer interfaces, improves the accuracy of medical diagnostics, or enhances the treatment of various medical disorders. Particular examples of the described biophysical sensing systems enable widespread use of neuro-feedback for numerous applications by reducing the cost, complexity, and preparation time of such procedures when compared to typical EEG, MEG, and other medical imaging systems.

It is to be appreciated that embodiments of the methods and systems discussed herein are not limited in application to the details of construction and the arrangement of components set forth in the following description or illustrated in the accompanying drawings. The methods and systems are capable of implementation in other embodiments and of being practiced or of being carried out in various ways. Examples of specific implementations are provided herein for illustrative purposes only and are not intended to be limiting. Also, the phraseology and terminology used herein is for the purpose of description and should not be regarded as limiting. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. Any references to front and back, left and right, top and bottom, upper and lower, and vertical and horizontal are intended for convenience of description, not to limit the present systems and methods or their components to any one positional or spatial orientation.

Referring to FIG. 1, illustrated is one example of a contactless biophysical sensing assembly 100. In various examples, the contactless biophysical sensing assembly 100 ("sensing assembly" 100) includes a plurality of contactless electric field detectors 102 arranged in an array, control electronics 108 for each of the contactless electric field detectors 102, an electromagnetic shield 110, and a housing 104. As illustrated in FIG. 1, in some examples the housing 104 may be shaped to conform to the profile of a subject's body, such as the head of the subject 116. As further shown, the sensing assembly 100 may also include a padding 114 such that the housing 104 comfortably sits on the subject 116 (e.g., the head of the subject 116). While shown in FIG. 1 as being positioned over the head of a subject 116 to detect bio-electrical signals generated by the brain of the subject, it is appreciated that in other examples, the sensing assembly 100 may be designed to detect biophysical signals generated by other areas of the body of the subject 116, such as the heart, nerves, or muscles, to name a few examples.

In various examples, the housing 104 encloses the various components of the sensing assembly 100, such as the array of contactless electric field detectors 102, the control electronics 108, and the electromagnetic shielding 110. The housing 104 provides structure and supports the various components of the sensing assembly 100. FIG. 1 illustrates one example in which the housing 104 is a headpiece shaped as a helmet. However, in other examples, the housing 104 is not so limited and may be shaped according to the body part proximate the electric field desired to be measured. For instance, the housing 104 may include a wrap that is wrapped around a head, limb, or torso of a user or patient. Or, in other examples, the housing 104 may take the form of an object that supports or is positioned immediately proximate the subject 116, such as a chair or table.

As shown in FIG. 1, the helmet may have an outer surface 106 that is formed from an impact resistive material or materials, such as a hard plastic, polymer, reinforced fiberglass, Kevlar, or carbon fiber, to name a few examples. The outer surface 106 protects the other components of the sensing assembly 100 from dust, dirt, moisture, impacts, and other external forces. In various examples, the outer surface 106 may include an aesthetically pleasing pattern or image to increase comfort and facilitate creating an enjoyable experience for the subject 116. While FIG. 1 illustrates one example of a helmet, it is appreciated that in various other examples other shapes may be used for the housing 104. For instance, the housing 104 may be shaped as a helmet for a sporting event, such as a football helmet, an ice hockey helmet, a motocross helmet, an auto-racing helmet, a motorcycle helmet, or a bicycle helmet, to name a few examples. In still other examples, the housing 104 may be formed from a material, such as elastic, cloth, or a netting material, that is configured to elastically conform to a profile of the subject 116, e.g., a profile of the subject's scalp.

Interposed between the outer surface 106 of the housing 104 and the control electronics 108 may be one or more layers of padding 114. For instance, the padding 114 may include a foam padding that further conforms the housing 104 to the body of the subject 116. In other examples, the padding 114 may include a rubber padding, a cloth padding, or any type of soft material. The padding 114 is positioned in between the outer surface 106 of the housing 104 and the control electronics 108 such that when the sensing assembly 100 is placed on the subject 116, the control electronics 108 and contactless electric field detectors 102 may be afforded space to conform to the profile of the body of the subject 116. That is, movement of the control electronics 108 and contactless electric field detectors 102 may compress the padding 114.

In various examples, the array of contactless electric field detectors 102 may be arranged to measure a spatial distribution of components of an electric field around the subject 116, which may be a user or a patient, for example. For example, each electric field detector 102 may be arranged to measure time varying electric fields generated by the brain, heart, nerves, or muscles. As discussed herein, each of the contactless electric field detectors 102 is "contactless" in the sense that it may be positioned physically proximate, but not in immediate contact, with the subject 116. That is, each electric field detector 102 is not required to contact the skin, scalp, or other surface of the body of the subject 116 to detect the corresponding electric field component. For instance, in contrast to the gel-based wet electrodes of a typical electroencephalographs, which must be physically placed on the scalp of a subject, various examples of the contactless electric field detectors 102 described herein do not need to be directly placed on the skin or scalp of a subject to perform the described sensing operations. For example, the housing 104 of the sensing assembly 100 may be configured to suspend each contactless electric field detector 102 relative to the subject 116 (e.g., the scalp or skin of the subject 116). For instance, each contactless electric field detector 102 may be suspended by the padding 114 or the electromagnetic shield 110. In addition to avoiding subject discomfort, such an arrangement also avoids noise artifacts that may result from electrical impedance changes associated with subject 116 movement, sweating, and/or environmental factors. In practice, while not required, the one or more contactless electric field detectors 102 may in fact temporarily contact or rest against the subject 116. Similarly, the housing 104 may rest against the subject 116. While described as "contactless", incidental contact with the subject 116 will not disturb or effect the operation of the contactless electric field detectors 116.

As shown in FIG. 1, in various examples, the array of contactless electric field detectors 102 may be arranged in a uniform pattern to substantially cover a desired area on the body of the subject 116. While shown in FIG. 1 in a cut-away view, it is appreciated that in the illustrated example the array of contactless electric field detectors 102 are arranged to substantially cover the scalp of the subject 116. That is, the illustrated array of contactless electric field detectors 102 are positioned outside the head of the subject 116. In one example, the contactless electric field detectors 102 are arranged in a grid pattern with an even spacing between each of the contactless electric field detectors 102. For instance, each of the contactless electric field detectors 102 may be closely spaced (approximately 1 cm apart) relative to the other contactless electric field detectors 102 to maximize the spatial resolution of the array. However, in other examples, the array of contactless electric field detectors 102 may be arranged in other patterns, and may be spaced with any suitable distance there between. In particular, the arrangement and spacing of the electric field detectors 102 may depend on the particular biophysical signal that is desired to be sensed and/or the location of placement of the contactless electric field detectors 102 on the body. While shown in FIG. 1 as an array, it is appreciated that in certain other examples a single contactless electric field detector 102 may be used in place of an array.

In various examples, each contactless electric field detector 102 of the illustrated array may be a single or multi-axis microelectromechanical system (MEMS) electric field detector configured to sense a vector component of the electric field. That is, in certain examples, component of the electric field detected by each of the contactless electric field detectors 102 is a vector having a direction and an amplitude at a position corresponding to the particular contactless electric field detector 102 that detected that vector component. However, in other examples, the component may include just a scalar magnitude or just a scalar direction. Each contactless electric field detector 102 may be continuously operated to provide a continuous stream of sensed measurements (i.e., electric field component measurements). Each of the contactless electric field detectors 102 may include a charge source (e.g., an electric dipole source) coupled to a suspended proof mass, and may detect the corresponding component of the electric field based on displacement (e.g., deflection or torsional movement) of the proof mass. The charge source may include any suitable source of a semi-permanent static electric dipole, such as an electret or a capacitor plate having a residual free charge and/or polarization. The induced electric dipole causes motion of the proof mass when exposed to the electric field. Accordingly, the motion may be detected to sense the corresponding component of the electric field.

For instance, one or more of the contactless electric field detectors 102 may sense a corresponding component of the electric field based on a measured capacitance variation due to movement (e.g., torsional movement) of the proof mass. However, in another example, one or more of the contactless electric field detectors 102 may sense a corresponding component of the electric field based on a measured frequency variation due to movement of the proof mass. In another example, one or more of the contactless electric field detectors 102 may sense a corresponding component of the electric field based on a measured optical deflection due to movement of the proof mass. Particular examples of MEMS contactless electric field detectors 102 that may be used within the array of contactless electric field detectors 102 shown in FIG. 1 are further illustrated and described below with reference to at least FIGS. 5A-7. While in one example, each contactless electric field detector 102 may be independently operated to measure a component of the electric field, in certain other examples, each contactless electric field detector 102 of the array may be coupled to the other detectors 102 within the array such that received electric field signals are coherently amplified.

Each of the contactless electric field detectors 102 of the illustrated array may be electronically coupled to corresponding control electronics 108. The control electronics 108 may include an integrated circuit that provides sensor data based on the electric field component sensed by the corresponding contactless electric field detector 102. For instance, the control electronics 108 may include an analog to digital converter. Each analog to digital converter may receive an output from the corresponding contactless electric field detector 102, the output being an analog signal representative of the component of the electric field sensed by the corresponding contactless electric field detector 102. Each analog to digital converter may convert the received analog signal to a digital signal and provide the sensor data to a control system (not shown in FIG. 1). In some examples, the control electronics 108 may include one or more auxiliary sensors co-located with the corresponding contactless electric field detector 102 and positioned to detect one or more external influences that may introduce noise, may distort, or may otherwise adversely affect the measurement of electric field components.

In one example, the auxiliary sensor may include an inertial sensor positioned proximate at least one contactless electric field detector 102 of the array of contactless electric field detectors 102 to sense movement of the subject 116. For instance, the control electronics 108 may include an accelerometer to measure accelerations that can be used to compensate for motion induced effects in the sensed electric field component. In other examples, the control electronics 108 may include at least one additional electric field detector to sense an external electric field. That is, while the array of contactless electric field detectors 102 may be positioned to sense electric field components of the electric field generated by the subject 116 (e.g., a brain of the subject 116), the additional electric field detector may be used to detect a component of an electric field external to the subject 116. The additional electric field detector may be similar to the contactless electric field detectors 102 and may include the example electric field detectors discussed below with reference to at least FIGS. 5A-7. An output of the additional electric field detector may be used to compensate for effects on the sensed electric field component of the subject's electric field. In various other examples, the control electronics 108 may include other types of sensors (e.g., temperature sensors, eye trackers, physiological sensors, cameras, magnetometers, chemical sensors, environmental sensors, and etc.) that measure parameters that may introduce errors in the intended bio-electrical measurement. For instance, a physiological sensor may be included within the control electronics 108 and may sense physiological characteristics of the subject 116 (e.g., temperature, sweating, restlessness, etc.).

As shown, the control electronics 108 of each contactless electric field detector 102 may be electrically coupled via one or more electrical connections 112 (e.g., wires, electrical leads, etc.). While not explicitly illustrated in FIG. 1, in various examples, the electrical connections 112 may further couple the control electronics 108 to a control system. One example of a control system for the sensing assembly 100 is discussed with reference to FIG. 2.

Interposed between the control electronics 108 and the contactless electric field detectors 102 is an electromagnetic shield 110. The electromagnetic shield 110 is positioned to electromagnetically isolate the array of contactless electric field detectors 102 from electromagnetic interference from the control electronics 108, and other sources of electromagnetic interference (e.g., a 60 Hz power line noise). Such an arrangement isolates the array of contactless electric field detectors 102 from interfering effects which may arise from the operation of the control electronics 108 to control the array of contactless electric field detectors 102. The electromagnetic shield 110 is illustrated in FIG. 1 as a layer of continuous electromagnetic shielding. For example, the electromagnetic shield 110 may be a Faraday cage or other electrically ground conductive material. In some examples, the electromagnetic shield 110 is composed of a flexible material such that, along with the array of contactless electric field detectors 102, the electromagnetic shield 110 conforms to the profile of the subject's body. For instance, FIG. 1 illustrates the electromagnetic shield shaped to the profile of the subject's head. In this regard, the electromagnetic shield may be formed as a net.

Figure 2:
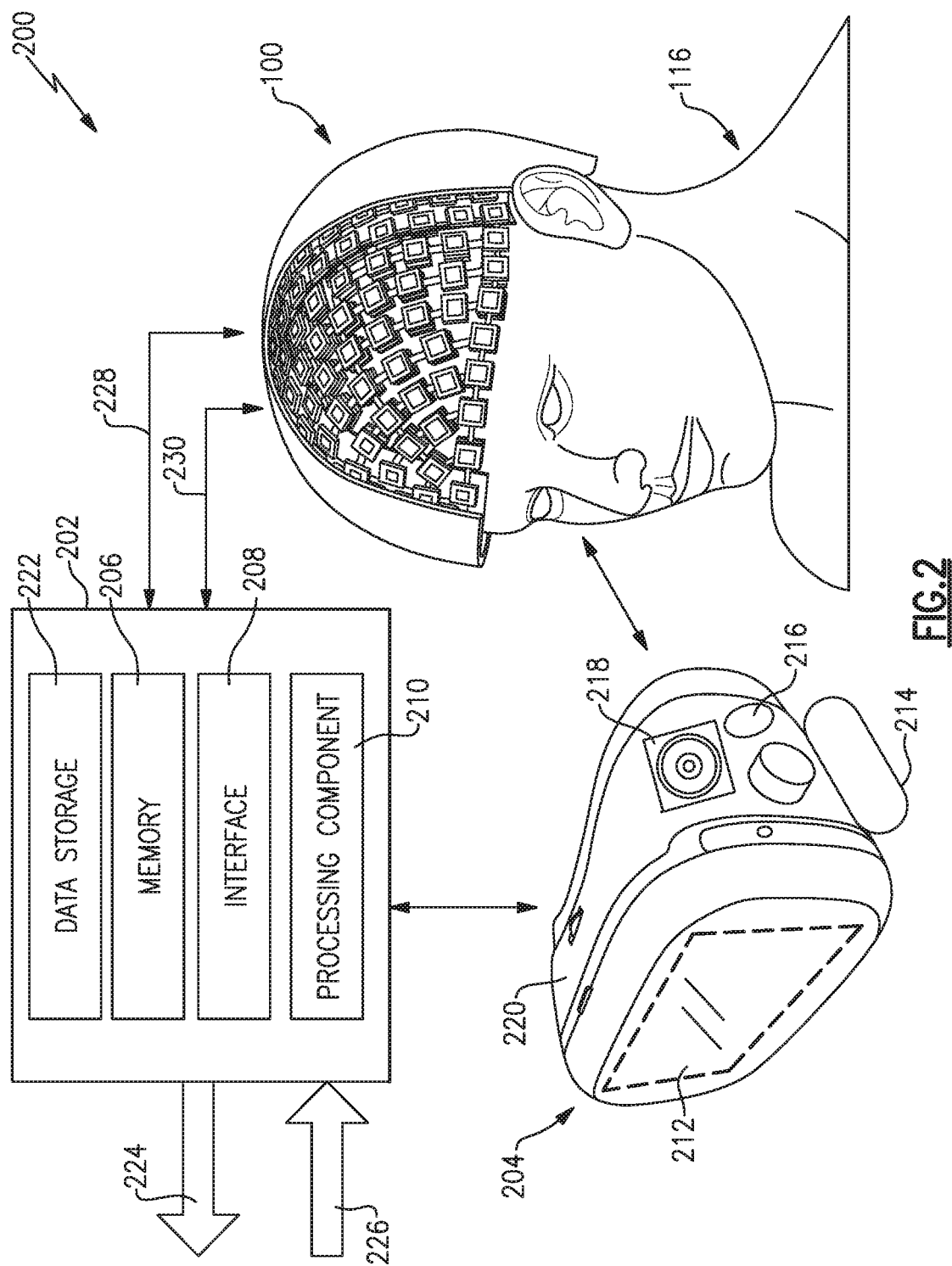
FIG. 2 is a biophysical sensing system that includes the biophysical sensing assembly of FIG. 1, according to various examples described herein.

In various examples, the biophysical sensing assembly 100 may be incorporated within a biophysical sensing system. Such a system may receive and utilize sensor data from the biophysical sensing assembly 100 to provide advancements in education and training, human-machine interfaces, medical diagnostics, and treatment of medical disorders, among the various other fields described below. FIG. 2 illustrates one example of a biophysical sensing system ("sensing system" 200). In various examples, the sensing system 200 may include the sensing assembly 100 illustrated in FIG. 1, a control system 202, and a feedback system 204, among other components. FIG. 2 is described with continuing reference to FIG. 1.

As shown, the control system 202 may be coupled to the sensing assembly 100 and the feedback system 204. While shown as a separate component from the sensing assembly 100 and the feedback system 204, in various other examples the control system 202 may be integrated within the housing 104 of the sensing assembly 100, integrated within a housing 220 of the feedback system 204, or integrated within a shared housing between the sensing assembly 100 and the feedback system 204. For instance, in one example, the control system 202 and the feedback system 204 are both integrated within the headpiece of the sensing assembly 100 illustrated in FIG. 1.

In various examples, the control system 202 may include one or a combination of, analog circuitry, digital circuitry, or one or more microprocessors executing software instructions (e.g., predefined routines). In FIG. 2, the control system 202 is shown as having at least a memory 206, a communication interface 208 (e.g., system interface), data storage 222, and a processing component 210. The processing component 210 may be a Central Processing Unit (CPU) of a computing system or a Digital Signal Processor (DSP) that is configured to execute the processes described herein as generally being performed by the control system 202. However, in other examples, the processing component 210 may include a Field Program Gate Array (FPGA) or an Application-Specific Integrated Circuit (ASIC). For example, the FPGA may include an array of programmable logic blocks (including logical cells) that are specified to perform the various steps, acts, and functions described herein with reference to the control system 202.

Each of the memory 206, system interface 208, data storage 222, and the processing component 210 may be coupled by an interconnection element such as a bus or other connection for exchanging data and/or instructions. Unless otherwise indicated, signal lines between components of the control system 202, components of the sensing assembly 100, and components of the feedback system 204 may be implemented as discrete analog or digital signal lines. The memory 206 and/or data storage 222 stores data, a series of instructions (e.g., routines), and/or one or more programs that are coded to be executed by the processing component 210. The processing component 210 may access and execute the series of instructions (e.g., routines), and/or one or more programs to perform the various processes described herein as performed by the control system 202. Some of the processing operations performed by the control system 202 may be expressed in terms of calculations, determinations, or estimations by the control system 202, a component of the control system 202, or one or more components, engines, or modules executed by the control system 202. The equivalent of calculating, determining, or estimating, can be performed by any suitable analog or digital signal processing techniques and are included within the scope of this disclosure. In one particular example, the control system 202 is a computing system. One example of a computing system is further described herein with reference to FIG. 10. While the control system 202 is illustrated as a single control system in FIG. 2, it is appreciated that in various other examples the control system 202 may instead be a network of control systems, or a network of computing devices collectively executing a shared control routine. For instance, in some examples, the control system 202 may be implemented as a plurality of cloud instances executing on a cloud computing system.

Referring to FIG. 2, the control system 202 is coupled and in electrical communication with the sensing assembly 100 via the control electronics 108 of the sensing assembly 100. Specifically, the control system 202 may be coupled to the control electronics 108 through a wired connection (e.g., one or more electrical cables) or a wireless connection (e.g., a short range piconet, such as Bluetooth). The control electronics 108 may send and receive one or more digital or analog signals with the control system 202 via the system interface 208. For instance, the control system 202 may communicate with the control electronics 108 via the system interface 208 to receive sensor data (e.g., shown as arrow 228) from the control electronics 108, to receive auxiliary sensor data (e.g., motion data, external electric field data, and/or temperature data) (e.g., shown as arrow 230) from the control electronics 108, to send one or more control signals to the feedback system 204, and/or to send one or more control signals to the control electronics 108. The system interface 208 may include one or more input devices, one or more output devices, or a combination of input and output devices. As further described herein, in many instances the control system 202 may further communicate (e.g., send and receive instructions and/or data) with one or more external entities, such as users, external computing systems, external feedback interfaces, additional biophysical sensing systems, and databases via the system interface 108.

During the operation of the sensing assembly 100, the control system 202 may receive sensor data from the control electronics 108 in real time as each contactless electric field detector 102 continuously or discretely measure the electric field components of a time varying electric field of the subject 116. As discussed above, in many instances this is an electric field generated by the brain of the subject 116. Upon receiving the sensor data, the control system 202 may buffer and/or filter the sensor data prior to performing one or more operations to generate an estimate of the electric field. As discussed with reference to FIG. 1, in various examples the control electronics 108 may include one or more auxiliary sensors (e.g., inertial sensors, additional electric field detectors, temperature sensors, physiological sensors, etc.) to detect one or more external influences that may introduce noise, may distort, or may otherwise adversely affect the electric field components sensed by the array of contactless electric field detectors 102. Accordingly, in addition to the sensor data, the system interface 208 may receive auxiliary sensor data from the control electronics 108.

Based on the received sensor data and the received auxiliary sensor data, the control system 202 may filter the sensor data to remove the effects that the external influence(s) may have on the sensor data. For instance, the control system 202 may include one or more filters that are applied to the sensor data to remove the effects of vibration, body motion, external electric fields, physiological effects, and/or other influences on the sensor data. Specifically, an influence on the sensor data may be removed by subtracting the sensed auxiliary data from the sensor data based on a previously determined scale factor associated with each error term in the auxiliary sensor data. Alternatively, each of the contactless electric field sensors 102 may be continuously or periodically recalibrated by comparing the sensor data to known fiducials and/or statistical behavior. External data inputs from the auxiliary sensors, or other knowledge of the environment, can help establish fiducial references for this purpose. For example, a camera may provide knowledge of body motion of the user.

In various examples, the control system 202 generates an estimate of the sensed electric field based at least in part on the sensor data received from the control electronics 108. That is, the control system 202 generates the estimate of the electric field based on the collective electronic field vector component measurements of each contactless electric field detector 102 of the array. In various examples, each measured electric field vector component is temporally aligned to generate a spatial distribution of the electric field at that given time. That is, the position of each contactless electric field detector 102 is mapped to a location within the estimate of the electric field (e.g., relative to a position of the electric field detectors 102 on the subject). The corresponding sensed electric field vector component by each contactless electric field detector 102 is representative of a direction and an amplitude (or scalar magnitude) of the electric field at that corresponding location. For instance, the sensor data may be used for Electric Field Encephalography (EFEG) processes to estimate electric field activity of the subject 116 (e.g., the subject's brain). While in one example, snapshots (e.g., instantaneous measurements) may be used to estimate the electric field at a desired moment in time, in certain other examples, the control system 202 may continuously generate an electric field estimate as sensor data is continuously received. As such, in some examples, the estimate of the electric field is a time varying spatial distribution of the electric field. Such an example permits the control system 202 (or a user) to track temporal changes in the electric field in response to one or more subject stimuli.

Figure 11A:
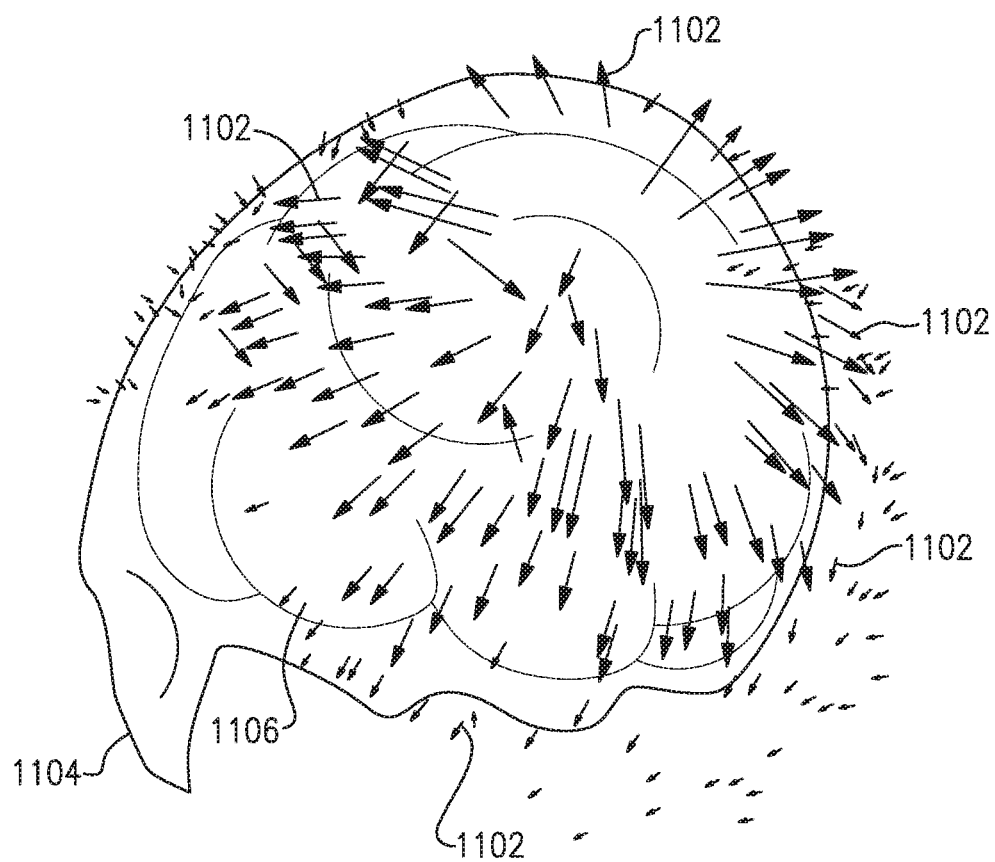
FIG. 11A is a spatial distribution of electric field vector components as may be detected by the biophysical sensing assembly of FIG. 1, according to various examples discussed herein.
Figure 11B:
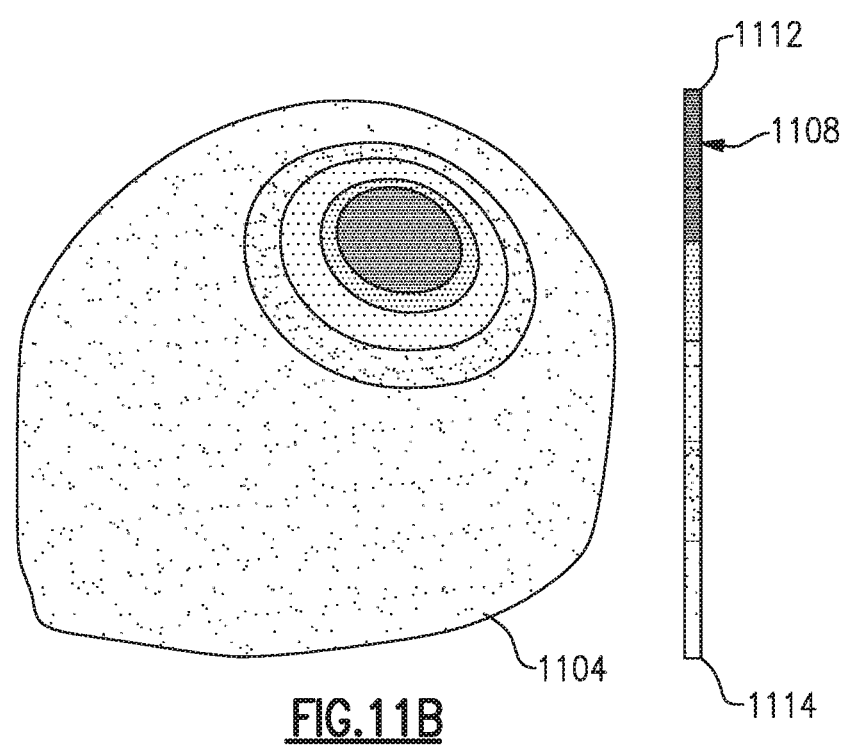
FIG. 11B is a heatmap of a voltage induced by an electric dipole corresponding to the electric field vector components illustrated in FIG. 11A.
Figure 11C:
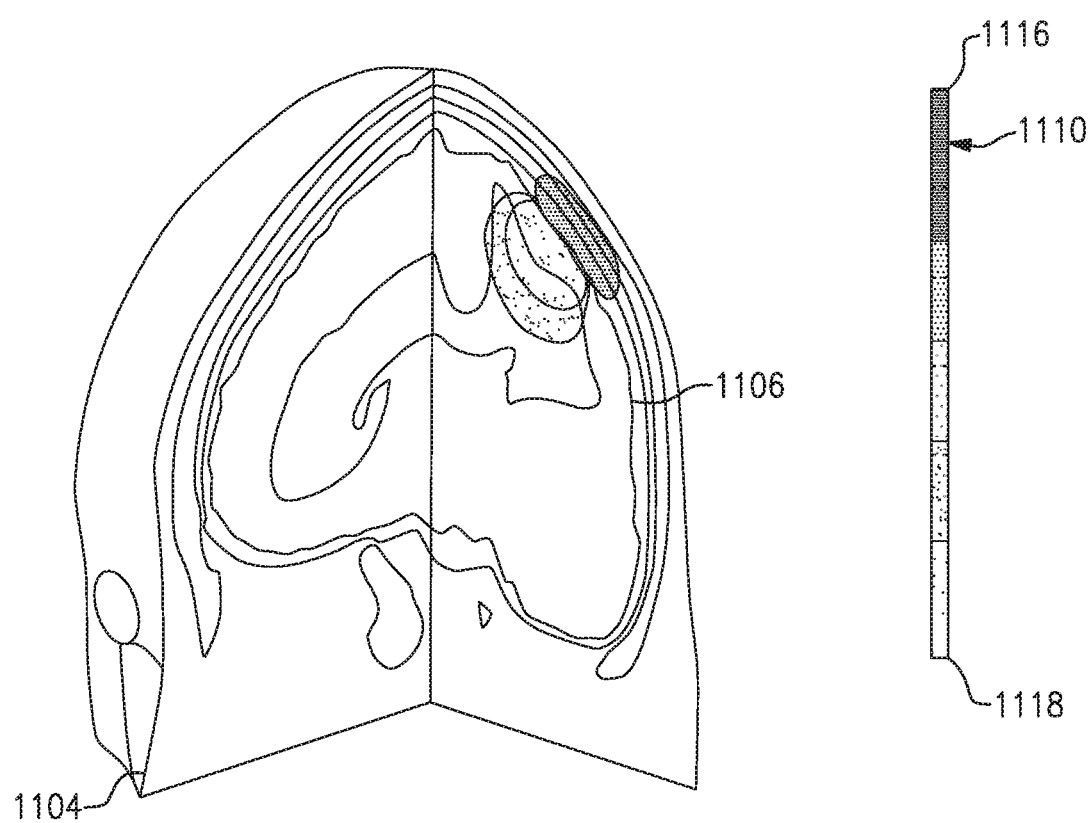
FIG. 11C is another heatmap of a voltage induced by an electric dipole corresponding to the electric field vector components illustrated in FIG. 11A.

Referring to FIG. 11A, illustrated is one example of a spatial distribution of electric field vector components as may be observed by the array of contactless electric field detectors 102 described herein with reference to at least FIG. 1 and FIG. 2. In particular, in FIG. 11A each vector component is illustrated by an arrow 1102 relative to a head 1104, which may be the head of the subject 116 shown in FIG. 1 and FIG. 2. In FIG. 11A, each vector component corresponds to an electric dipole within a brain 1106 of the head 1104. Specifically, the electric field is the gradient of the voltage distribution. FIG. 11B illustrates a heat map of the voltage induced by electric dipole source when observed from the surface of the head 1104. In FIG. 11B, a heat scale 1108 illustrates the voltage magnitude induced from the electric dipole. A first end 1112 of the heat scale 1108 represents a high magnitude, and a second end 1114 of the heat scale 1108 represents a low magnitude. FIG. 11C illustrates a heat map of an internal view of the voltage distribution induced by the electric dipole. In particular, FIG. 11C is a cut-away view of the head 1104. In FIG. 11C, a heat scale 1110 illustrates the magnitude of the voltage induced by the electric dipole source. A first end 1116 of the heat scale 1110 represents a high magnitude, and a second end 1118 of the heat scale 1110 represents a low magnitude.

Returning to FIG. 2, as discussed herein, in many instances the sensor data collected by the sensing assembly 100 may be utilized to advance education and training, improve human-machine interfaces, increase the accuracy, speed, and efficiency of medical diagnostics, and improve the treatment of medical disorders. These are just a few examples, and as further discussed below, the described sensing system 200 may be used to provide benefits in many other fields.

In one example, the control system 202 may compare the estimate of the electric field to an electric field template of a mental state. For instance, the mental state may include a mental state indicative of a neurological condition, such as ADHD, autism, dyslexia, depression, or insomnia, to name a few examples. In another example, the mental state may include a mental state indicative of a behavior, such as concentration, impulsivity, or anxiety, to name a few examples. In still other examples, the mental state may be a mental state indicative of a medical condition, such as a concussion to various neurodegenerative diseases. In further examples, the mental state may include a behavior mental state, such as concentration, restlessness, or tiredness. However, in other examples, the mental state may include an emotional mental state, such as happiness, anger, frustration, sadness, etc. Similar to the estimate of the electric field, the template may be composed of various vector components of an electric field corresponding to that mental state. Templates may be stored, at the data storage 222 or otherwise made available to the control system 202 at an external database. Accordingly, comparison between the estimate of the electric field and the template may include comparing one spatial distribution of electric field vector components to another spatial distribution of vector components. For example, the control system 202 may use various EFEG processing techniques to compare the estimate of the electric field to the electric field template, and in some examples, determine a difference between the estimate of the electric field and the electric field template.

Based on the comparison to the template, the control system 202 may provide a diagnosis, may provide additional information, may control the sensing assembly 100 to perform additional sensing operations on the subject 116, and/or may provide feedback to the subject 116 or an external entity. In particular examples, the control system 202 may provide one or more control signals to the feedback system 204 to provide feedback to elicit a desired response from the subject 116. For example, the control system 202 may control the feedback system 204 to provide feedback to induce a neural response in the subject 116 based on a difference between the estimate of the electric field and the template. The particular feedback provided may depend on the determined distance between the estimated electric field and the template. For instance, feedback may be specifically tailored for each sensed difference. In other examples, to control system 202 may control the feedback system 204 to drive the electric field of the subject 116 to match the template. That is, the control system 202 may control the feedback system 204 such that a subsequent estimate of the electric field substantially matches the template.

As illustrated in FIG. 2, in various examples, the feedback system 204 may include a housing 220 that is configured to attach to the body of the subject 116. While in one example the feedback system 204 may be integrated within the housing 104 of the sensing assembly 100, in the illustrated implementation, the feedback system 204 has a separate housing. In particular, FIG. 2 illustrates the feedback system 204 as including a goggle housing. In various examples, the feedback system 204 may include one or more feedback interfaces to provide active, passive, or indirect behavioral feedback to the subject 116. For example, the one or more feedback interfaces may include various types of hardware, and/or hardware combined with software, to provide visual, auditory, haptic, heating and/or cooling, and/or chemical feedback (e.g., olfactory feedback) to the subject 116. In FIG. 2, the feedback system 204 is shown as including a visual display 212, a speaker 218, and/or a haptic transducer 214 (e.g., a vibration motor). However, in other examples, other types of feedback interfaces may be included within the feedback system 204. For instance, the feedback system 204 may include a heating or cooling source and/or chemical source, to name a few examples. In other examples, the feedback system may include one or more active feedback interfaces such as the illustrated active stimulator 216.

In the illustrated example, the housing 220 includes a visual display 212 positioned on an interior surface of the housing 220 such that when the housing 220 is positioned over the eyes of the subject 116 the visual display 212 is visible to the subject 116, or directs an optical image at the subject 116, within the housing 220. The visual display 212 may include any suitable visual display screen, such as a liquid crystal display (LCD), plasma screen, or other mounted optical display. The housing 220 is further shown as including at least one speaker 218 and a haptic transducer 214. The speaker 218 is positioned on an exterior surface of the housing 220. In particular, the speaker 218 is positioned such that it is proximate to an ear of the subject 116 when the housing 220 is placed over the eyes of the subject 116. The haptic transducer 214 is positioned on the housing 220 such that it may provide haptic (tactile), pressure, or kinesthetic communication to the subject 116. For example, the haptic transducer 214 may include a Piezoelectric actuator. While shown as a goggle housing, it is appreciated that in various other examples the housing 220 of the feedback system 204 may take various other shapes and forms.

As discussed, in certain examples the feedback system 204 may include other types of feedback interfaces than those explicitly illustrated in FIG. 2. For instance, in one example the feedback system 204 includes a heating or cooling source that is positioned proximate the subject 116 to provide a controllable heating or cooling stimulus to the subject. In one example, the heating or cooling source may include an electrical heating pad or a chemical heating pad. In other examples, the feedback system 204 may include a chemical source, such as an olfactory stimulator or a drug dispenser. The olfactory stimulator may controllably provide smells to the subject 116, and the drug dispenser may controllably provide a drug or other chemical substance to the subject 116. For instance, the olfactory stimulator may include a pump coupled with a chemical reservoir. The aerosol pump may be controlled to disperse the contents of the chemical reservoir to the subject to provide a controlled chemical stimulus. Moreover, while the examples of the feedback interfaces are illustrated in FIG. 2 as being directly coupled to the housing 220 of the feedback system 204, in other examples, the feedback interfaces may be remotely positioned relative to the feedback system 204 and may communicate with the feedback system 204 via a wired or wireless connection. For instance, a heating or cooling source may be positioned on the back of the subject's neck, and may be coupled via a wire to the housing 220.

In various examples, the control system 202 is configured to provide one or more control signals to the feedback system 204 to operate the feedback interface(s) and provide feedback. For instance, the control system 202 may control the feedback system 204 to operate the least one of the visual display 212, the speaker 218, the haptic transducer 214, and/or the other examples of the feedback interfaces described herein to induce a neural response in the subject 116. In particular, the control signal provided to the feedback system 204 and the behavioral feedback provided to the subject 116 is dependent on the particular application of the sensing system 200. That is, the particular behavioral feedback provided to the subject 116 is largely dependent on the desired subject response. For example, in one implementation, the feedback system 204 may operate at least one of the visual display 212, the speaker 218, and the haptic transducer 214 to suppress or augment one or more neural oscillations within subject's brain. In one example, the neural oscillations are alpha waves. Alpha wave power has been established as an indicator of a level of alertness. Accordingly, in some examples, alpha wave supression (e.g., desynchronization) and/or augmentation (e.g., synchronization) may be controlled to influence cognitive performance of the subject 116. In particular, alpha wave supression and/or augmentation may be tailored to the particular task performed by the subject 116. For instance, synchronization may inhibit other brain activity and may help in tasks requiring short term working memory, whereas desynchronization may assist information processing. In certain other examples, the feedback system 204 may operate at least one of the visual display 212, the speaker 218, and the haptic transducer 214 to modify an evoked potential in the subject 116. For example, the evoked potential may include a P300 evoked potential. It has been shown that a P300 evoked potential can indicate that a recognition or that something has been understood by a subject. Such an implementation can be used to influence or sense the pace or difficulty of a training program or other activity. The contactless electric field detectors 102 described herein enhance the signal-to-noise ratio such that the need for averaging multiple runs to measure an evoked potential (as required by typical approaches) can be reduced or eliminated.

For example, a neural oscillation pattern or other behavior can be induced in the subject 116 by providing feedback via the feedback system 204 to train the subject 116 to reach a desired type of brain activity. For example, the feedback system 204 may operate the visual display 212 to vary a size, shape, position, or other characteristics of an image on the visual display 212 to encourage the subject 116 towards an electric field estimate that matches an electric field template of a mental state. In some examples, the visual display 212 may be controlled in the form of a game, where the subject 116 must determine a certain outcome on an image in the visual display 212. The image may correspond to one or more dimensions of a brain state as measured by the array of contactless electric field detectors 102. Auditory (e.g., tones), haptic (e.g., vibrations or pressure sensations), heating and/or cooling, and/or chemical stimuli can provided in a similar manner. Visual, auditory, haptic feedback, heating and/or cooling, and chemical feedback may be applied independently, but may also be used together to complement one another or provide additional degrees of freedom.

In various examples, the control system 202 determines the optimum feedback based on the received sensor data, the desired subject 116 response, and the hardware (e.g., feedback interface(s)) available at the feedback system 204. For instance, the control system 202 may include one or more adaptive control laws or adaptive control algorithms that are executed to determine the optimum feedback. In various examples, the particular feedback provided to the subject 116 (or provided to another system which interfaces with the subject 116) depends on the desired response of the subject 116 to the feedback. For instance, the control system 202 may execute one or more selection routines that evaluate the availability of feedback interfaces and selects a particular feedback interface or interfaces that are capable of providing feedback to the subject to elicit the desired response (e.g., enhanced learning). The control system 202 may then provide a control signal to the feedback system 204 to operate the selected feedback interface or interfaces to elicit the desired response from the subject 116 or an external system. As described, in various examples, the control system 202 may execute one or more learning algorithms that continuously learns and adapts the provided feedback based on continuously received sensor data. In this manner, the control system 202, sensing assembly 100, and feedback system 204 may operate as a feedback loop to drive the subject 116 to the desired response.

As discussed, while in some examples feedback may be passively applied to the subject 116, such as through one or more visual displays, auditory feedback, heating or cooling, a smell, or a vibration, in other examples, the feedback system 204 may include one or more active feedback interfaces, such as the illustrated active stimulator 216. In such an example, the feedback system 204 may receive instructions from the control system 202 to operate the active stimulator 216 to provide a stimulus to the subject based at least in part on the estimate of the electric field. The stimulus may then be provided to the subject 116 by the active stimulator. For example, the active stimulator 216 may include an electrical lead positioned to provide an electrical potential to the subject 116. In one particular example, the active feedback may be provided in the form of a transcranial stimulation with AC or DC current. However, in other examples other types of stimuli may be provided to the subject 116 by the active stimulator 216, such as magnetic fields, optical signals, or chemical stimuli. In some examples, chemical stimuli may include drugs or other chemical substances. In some examples, the array of contactless electric field detectors 102 may be operated to measure the brain state of the subject 116 before, during, and/or after the application of the feedback. The application of the feedback may then be modified adaptively to achieve the desired outcome. Similar to the other feedback interfaces described herein, while shown as integral to the housing 220, in other examples the active stimulator 216 may be removed from the housing 220 and may communicate with the feedback system 204 via a wired or wireless connection.

In various examples, the control system 202 may also provide an output and/or receive an input from a user or other systems based on the estimate of the electric field or the sensor data. For instance, the estimate of the electric field or sensor data may be provided as diagnostic information to a physician or other medical diagnostic equipment. For example, the sensor data may provide information to enable a diagnostic medical test to be performed on the subject 116. In certain other examples, the estimate of the electric field and/or the sensor data may be used to generate a control input for another device or system. For instance, the control system 202 may generate a control input (shown as control input 224) for human-machine interface (e.g., brain-computer interface) based at least in part on the estimate of the electric field. In certain examples, the control input 224 may be used in a video game or as one end of a cognitive link between physically separated individuals. In other examples, the control input for the human-machine interface may be an interface for a robotic device, such as robotic devices used for neuro-prosthesis.

In addition to providing an output, in various other examples the control system 202 may receive an input (shown as input 226 in FIG. 2) from an external source. For instance, the control system 202 may receive external feedback controls from a user or other computing system. The external feedback controls may include information from one or more external auxiliary sensors, information and/or inputs from a user, and/or subject data from an external database. Such information may be integrated with the sensor data from the sensing assembly 100 to provide comprehensive feedback instructions to the feedback system 204. In other examples, the particular feedback provided by the feedback system 204 may be entirely based on an external input. Such may be the case in a clinical setting where the input to the control system 202 may be a physician's instructions for treatment of a medical condition. In such an example, the control system 202 instructs the feedback system 204 to operate the various feedback interfaces based on the physician's instructions. In other examples, the input to the control system 202 may be instructions from a teacher that relate to material being learned. In still other examples, the input may include additional biophysical information, such as information from an MEG, MRI, or PET system.

In addition to the feedback interfaces, in some examples the feedback system 204 may include one or more auxiliary subject sensors similar to the auxiliary sensor(s) of the sensing assembly 100. Each of the auxiliary subject sensors may be positioned and configured to provide information about the subject 116, or an error source, as an input to the control system 202. For instance, the auxiliary subject sensors may include a blink detector, camera, or other physiological monitor that improves the ultimate ability to recover the electric field components from the sensor data by measuring an error source. Auxiliary subject sensor data can be used by the control system 202 to further correct the sensor data and account for the error sources. For instance, auxiliary subject sensor data from the auxiliary subject sensors may be provided to the control system 202 to perform filtering operations previously discussed. That is, the auxiliary subject sensor data may be used by the control system 202 in one or more pre-processing steps that remove motion, body, and other noise artifacts that may influence or corrupt the sensor data.

As discussed, examples of the biophysical sensing assembly 100 and biophysical sensing system 200 may enable advances in various fields and various technologies. The examples of these fields and technologies are not intended to be limiting, and are merely provided as few illustrative examples. Further examples of the applications and relevant technical fields and technologies are discussed below. These examples are discussed with continuing reference to FIG. 1 and FIG. 2.

In various examples, measuring brain patterns with the contactless sensing assembly 100 and system 200 of the present disclosure is beneficial in automotive applications. For instance, the sensing assembly 100 and sensing system 200 may be used by an automobile to sense passenger intent (e.g., intent to change a radio setting), detect fatigue, or detect a driver's attention or some other parameter relevant to a safe operation of the vehicle. Based on the collected sensor data, the vehicle may then be controlled to respond and properly address a sensed situation. Similar implementations may also be useful in different types of transportation, military or industrial-related environments, such as aircraft, train yards, or factories. For instance, brain patterns of a plant operator may be monitored to increase operational effectiveness and/or safety.

In other examples, measuring brain patterns with the biophysical sensing assembly 100 and control system 202 of the present disclosure is beneficial in educational and training applications. For instance, the sensing assembly 100 and sensing system 200 may be used to enhance a task that a subject is in the process of completing. In further examples, measuring brain patterns with the sensing assembly 100 and system 200 of the present disclosure is beneficial in situations where a state of mind is relevant. For instance, the contactless sensing assembly 100 and sensing system 200 of the present disclosure may be used during interrogation proceedings where a subject may be non-cooperative. In such situations, the sensing assembly 100 and the sensing system 200 of the present disclosure can be used to detect mal-intent, truthfulness (or lack thereof), and related behaviors.

Advertisers may also find the contactless sensing assembly 100 and sensing system 200 of the present disclosure useful to detect interest, attention, or other behaviors of a targeted audience. For example, the contactless sensing assembly 100 and sensing system 200 of the present disclosure may include a control law or algorithm that generates or controls adaptive advertising to best match the interests and desires of the subject. This may be beneficial to the subject for at least the reason that advertisers can avoid providing irrelevant information to a targeted audience. It may also be used to ensure the subject is not interrupted at a critical time, such as when they are asleep, or in a state that an advertisement would not be well received. Similarly, sensor data from the contactless sensing assembly 100 and sensing system 200 of the present disclosure may be useful in the optimizing how and when arbitrary information should be presented to a user. For example, the delivery of text messages, news, and relevant task information, to name a few examples, can be guided by the contactless sensing assembly 100 and sensing system 200 of the present disclosure to determine the best time and conditions for delivery.

While described herein in various examples as including contactless electric field detectors 102, it is appreciated that in other examples the contactless electric field detectors 102 may be replaced with contactless magnetic field detectors. For instance, the sensing assembly 100 shown in FIG. 1 and the sensing system 200 shown in FIG. 2 may each include an array of contactless magnetic field detectors. In particular, the contactless magnetic field detectors may detect small electromagnetic signals which emanate from equipment, vehicles, transmitters, or biophysical sources, such as the body of a subject. Similar to the contactless electric field detectors 102, each contactless magnetic field detector may be a microelectromechanical-based (MEMS-based) sensor which measures motion of a suspended proof mass to determine one or more components of a received magnetic field. For instance, in the examples of the contactless electric field detector 102 described below with reference to FIGS. 5A-7 the source of concentrated electrical charge may be replaced by a magnet or other magnetic source While in various examples the contactless electric field detectors 102 described herein may be incorporated within a wearable housing (e.g., the headpiece shown in FIG. 1) to sense biophysical signals generated by the body of a subject, in various other examples the housing may not be wearable or the sensors may be incorporated within a machine or other system. For example, the contactless electric field detectors 102 may be incorporated within an electric field tomography (EFT) system for imaging (e.g., medical imaging). EFT uses electric fields to obtain a two or three-dimensional image of an object. When compared to other imaging techniques, and in particular, other medical imaging techniques, EFT is advantageous because it does not expose the subject to harmful ionizing radiation. Ionizing radiation is often a risk associated with current fluoroscopic or computed tomographic (CT) medical imaging systems. Furthermore, in comparison to magnetic resonance imaging (MRI), EFT is more compact and considerably less costly (e.g., it does not require a cryogen containment vessel).

As such, in various examples, contactless electric field detectors, such as those discussed below with reference to FIGS. 5A-7 may be incorporated within an EFT system that does not require contact with a subject to generate medical images of the subject. In particular, the EFT system may generate images of a subject in which the tissue of the subject is differentiated by its relative electrical conductivity.

Figure 3:
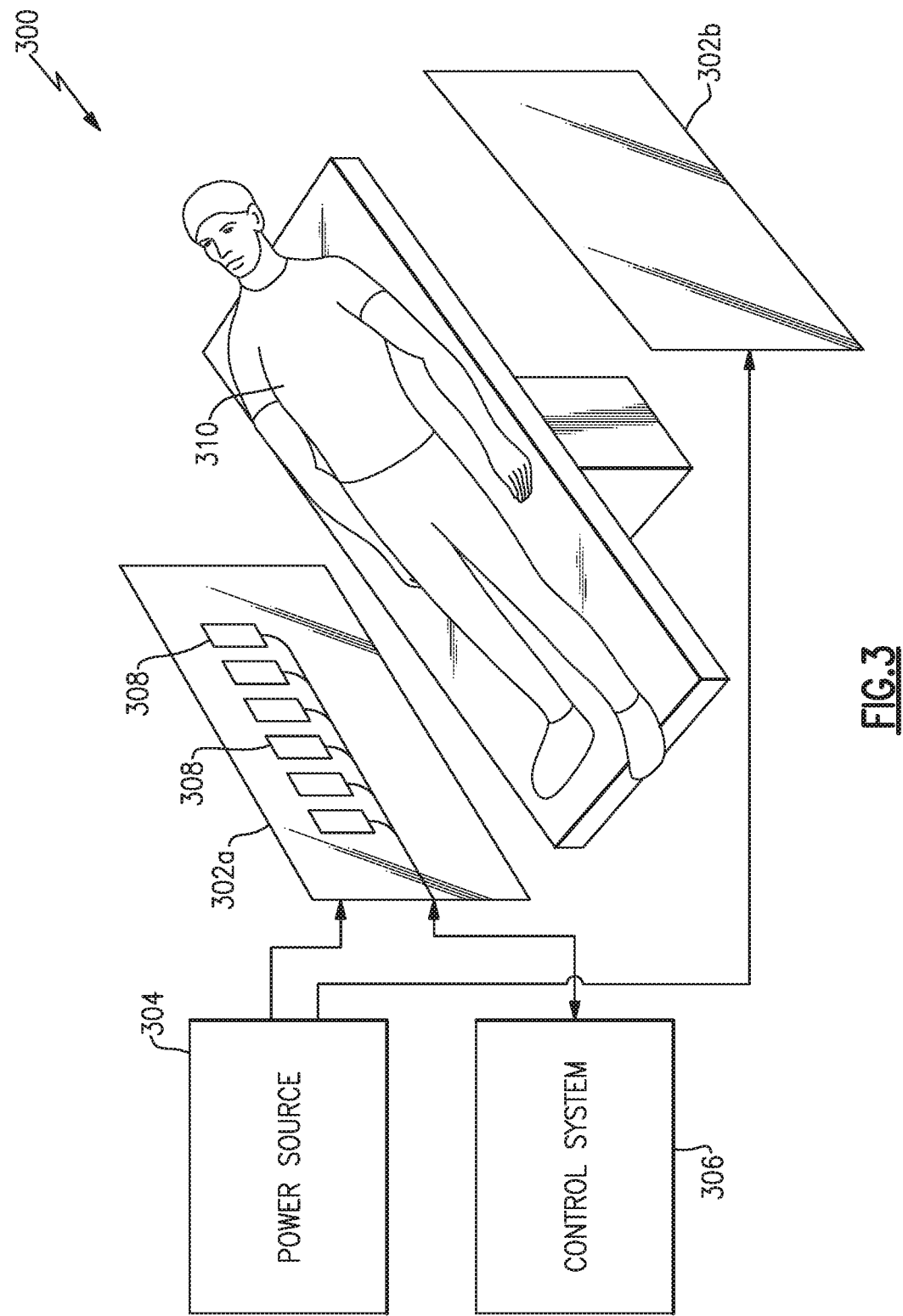
FIG. 3 is an electric field tomography (EFT) system, according to various examples described herein.

FIG. 3 illustrates one example of an EFT system 300 that incorporates one or more contactless electric field detectors 308. Each of the contactless electric field detectors 308 may be similar to those described above with reference to FIG. 1 and FIG. 2. Particular examples of the electric field detectors 308 are also further described below with reference to FIGS. 5A-7. As shown in FIG. 3, the EFT system 300 may include two or more electrodes 302a, 302b. The electrodes 302a, 302b may be spaced apart such that a subject 310 may be comfortably positioned between the pair of electrodes 302a, 302b. While shown in FIG. 3 as including two electrodes 302a, 302b, in practice, more than two electrodes may be used to substantially surround the subject 310 (or object). However, in some other examples, each of the electrodes 302a, 302b may be coupled to an actuator that is configured to displace the electrodes 302a, 302b and rotate the electrodes 302a, 302b about the subject 310. In some examples, the EFT system 300 may include a chair, table, or other surface at which the subject 310 is positioned. A power source 304 may also be coupled to each of the electrodes 302a, 302b.

As illustrated in FIG. 3, one or more arrangements of contactless electric field detectors 308 may be positioned about the body of the subject 310 (or object). FIG. 3 illustrates one arrangement of the contactless electric field detectors 308 positioned proximate a first of the two illustrated electrodes 302a. Each electrode 302a, 302b is configured to receive a voltage or current from the power source 304 and provide an electric field that passes through the subject 310. As will be appreciated by one of ordinary skill in the art, as the electric field passes through the body of the subject 310 it will be distorted by the dielectric properties of the body of the subject 310.

In various examples, the arrangement of contactless electric field detectors 308 are positioned to detect the distorted electric field in a manner similar to the electric field detectors 102 discussed above with reference to at least FIG. 1 and FIG. 2. By varying the orientation of the applied field relative to the subject 310, a large number of field measurements can be obtained from multiple angles. As further illustrated in FIG. 3, each of the contactless electric field detectors 308 may be coupled to a control system 306 and may provide sensor data based on the sensed electric field, which is distorted by the dielectric properties of the subject's body. Using tomographic reconstruction techniques (e.g., back projection), as will be appreciated by one or ordinary skill in the art, the control system 306 may generate an image of the interior of the subject's body based on the sensor data received from the arrangement of contactless electric field detectors 308.

Figure 4:
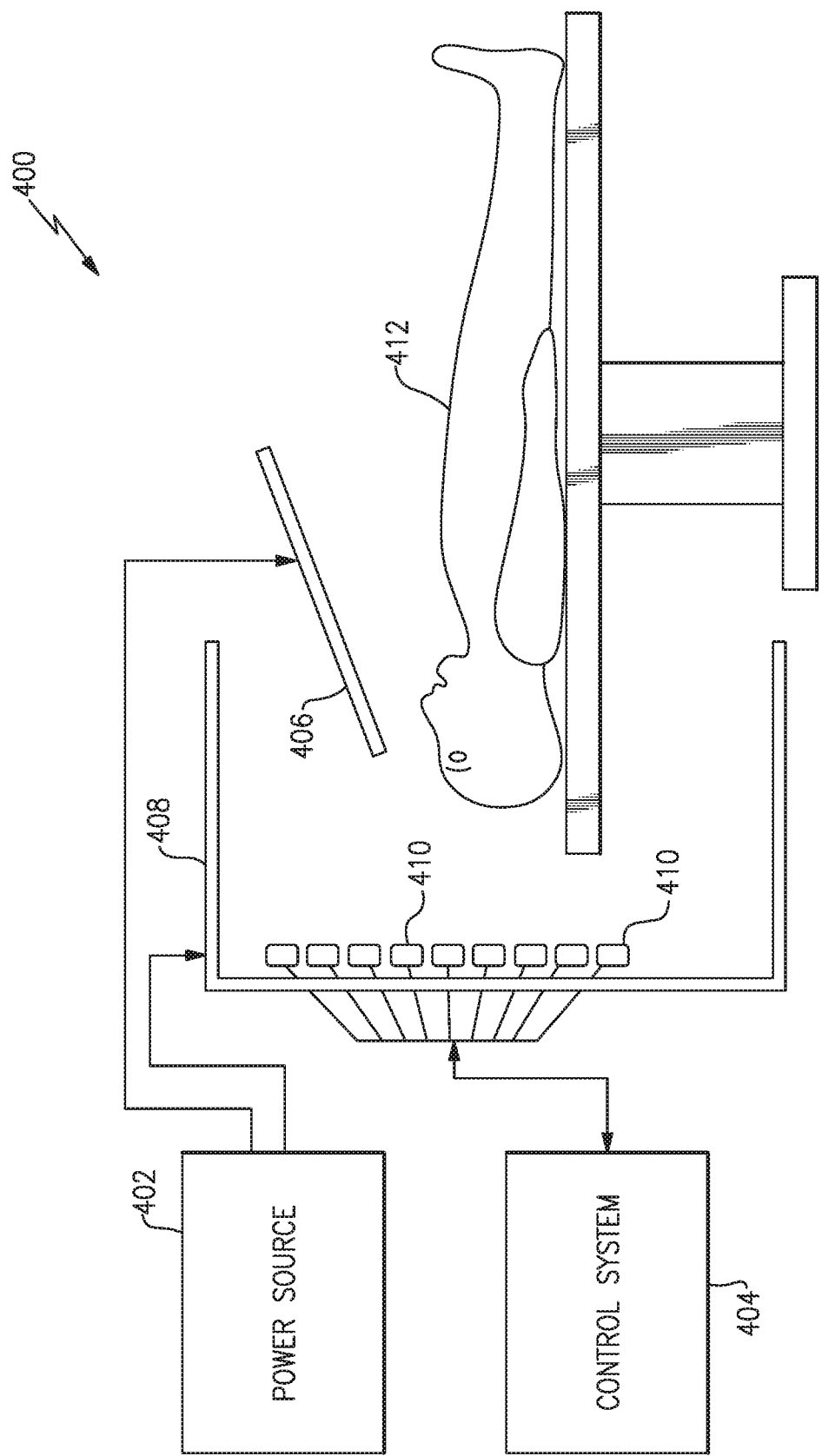
FIG. 4 is a surgical navigation system, according to various examples described herein.

In addition to imaging the body of the subject, in various examples, contactless electric field detectors may be incorporated within a system for tracking medical instruments. For instance, the contactless electric field detectors described herein may be incorporated within a surgical navigation system to accurately guide surgical instruments within a subject's body. One example of a surgical navigation system 400 that incorporates one or more contactless electric field detectors is illustrated in FIG. 4. Each of the contactless electric field detectors 410 may be similar to those described above with reference to FIG. 1 and FIG. 2. Particular examples of the electric field detectors 410 are also further described below with reference to FIGS. 5A-7.

Referring to FIG. 4, the surgical navigation system 400 may include a surgical instrument 406, an electrode 408, an arrangement of contactless electric field detectors 410, a power source 402, and a control system 404 (e.g., an instrument tracking system). Similar to the EFT system 300 described with reference to FIG. 3, the electrode 408 may be coupled to the power source 402 and may receive a voltage and/or current from the power source 402. Based on the received current or voltage, the electrode emits an electric field that passes through the subject 412. In various examples, the arrangement of contactless electric field detectors 410 are positioned to detect the electric field in a manner similar to that discussed above with reference to the electric field detectors 102 of FIG. 1 and FIG. 2. The sensor data from the arrangement of contactless electric field detectors 410 may be used by the control system 404 to generate an image of the body of the subject 412 and map a placement of the surgical instrument relative to the body. While shown outside the body in FIG. 4, it is appreciated that often the surgical instrument 406 may be within the body and, therefore, the image of the body may include a location of the surgical instrument 406 within the body.

In various examples, the surgical instrument 406 is electrically conductive and may be coupled to the power source 402 to receive a voltage and/or current from the power source 402. For example, the electrode 408 may be coupled to a first terminal of the power source 402 and the surgical instrument 406 may be coupled to an opposite second terminal of the power source 402. Such an implementation would remove the need to embed a transmitter or transmitting marker on the surgical instrument 406, which is often required by typical surgical instrument tracking systems. In various examples, the electric field between the surgical instrument 406 and the electrode 408 depends on the position and orientation of the surgical instrument 406. Accordingly, the arrangement of contactless electric field detectors 410 may sense the electric field to detect the position and orientation of the surgical instrument 406. In particular, based on the sensor data from the arrangement of contactless electric field detectors 410 the control system 404 may determine the position and orientation of the surgical instrument 406 relative to the subject 412. While not shown in FIG. 4, the surgical navigation system 400 may further include a conductive shield that fully encloses the other components of the surgical navigation system 400.

In various examples, the position and orientation of the surgical instrument 406 may be tracked in real time by the control system 404. The control system 404 may also be configured to directly guide or provide one or more instructions to guide a placement of the surgical instrument 406 based on the received sensor data. Such an implementation may be useful for at least the reason that the sensor data may be used to generate images of features that are invisible to the naked eye. In some examples, the source and receiver configuration illustrated in FIG. 4 may also be reversed for some applications. That is, one more signal sources can be located outside the body of the subject 412 while a packaged electric field detector is placed within the body. The electric field detector can be wired, in active surgical scenarios, or enclosed entirely by the body. The implanted electric field detector may provide information to a co-located device or wirelessly transmit the sensed sensor data to an external receiver.

Figure 5A:
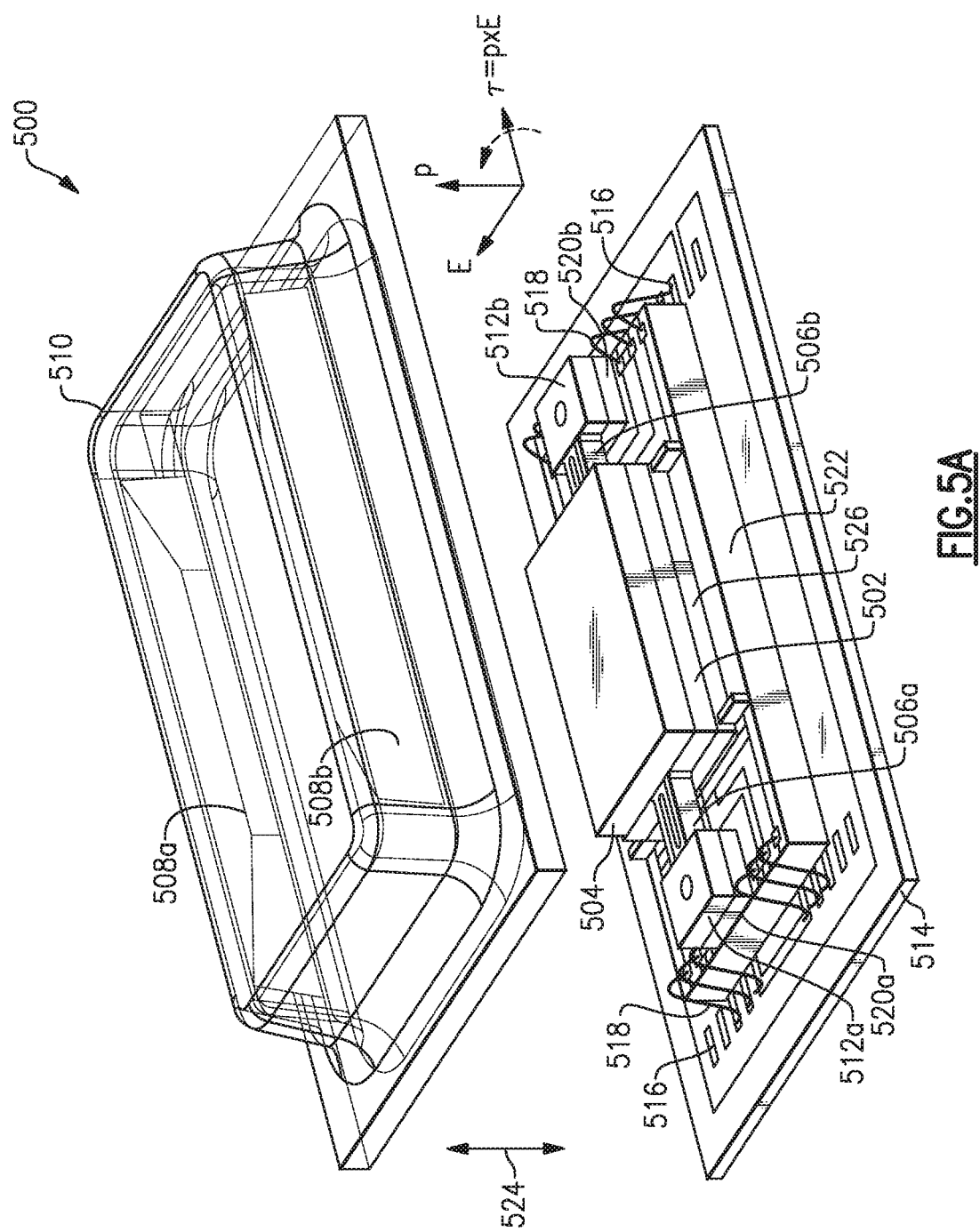
FIG. 5A is a perspective view of an electric field detector, shown with a cover detached from the detector, according to examples discussed herein.
Figure 5B:
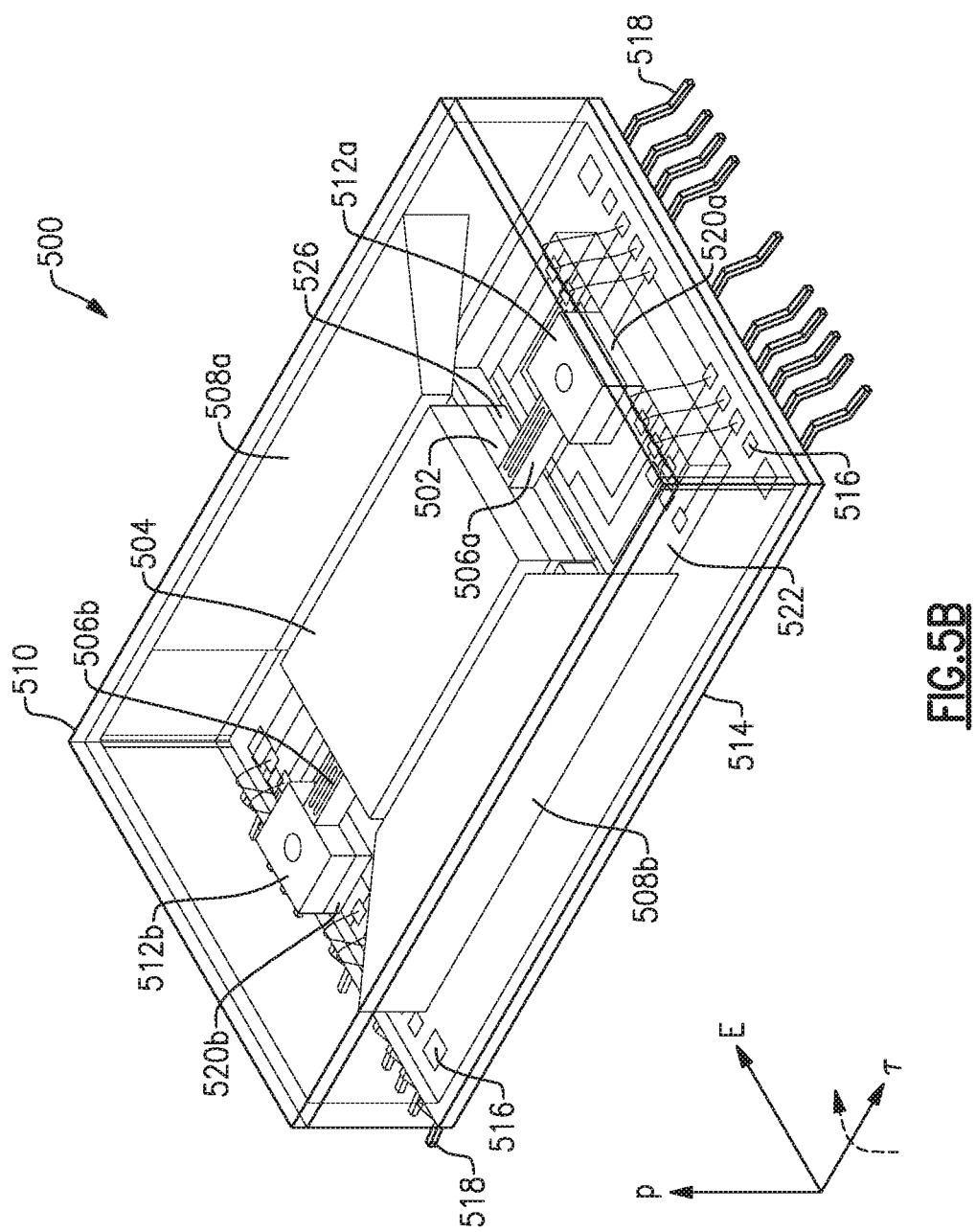
FIG. 5B is perspective view of the electric field detector illustrated in FIG. 5A with the cover attached, according to examples discussed herein.

Referring to now to FIGS. 5A and 5B illustrated are a perspective view of a contactless electric field detector 500 (also referred to as "electric field detector" 500) according to various examples described herein. FIG. 5A illustrates a view of the detector 500 with a cover 510 detached from the detector 500, and FIG. 5B shows a view of the detector 500 with the cover 510 attached. The cover 510 may be removed in a vertical direction (e.g., direction 524), as shown in FIG. 5A. In FIGS. 5A and 5B, the electric field detector 500 includes a microelectromechanical-based (MEMS-based) resonator, which may be defined by processing a structure wafer (e.g., a Silicon-on-Insulator wafer) to a desired geometry. As shown, the detector 500 may include a proof mass 502 coupled to a source of concentrated charge 504, a plurality of supports 506a, 506b (collectively "supports 506") one or more flux concentrators 508a, 508b (collectively "flux concentrators 508"), a cover 510, one or more anchors 512a, 512b, a baseplate 514, one or more electrical contacts 516, one or more leads 518, and a substrate 522, among other components.

While not shown in FIGS. 5A and 5B, each of the contacts 516 may couple the electric field detector 500 to a control circuit, such as the control electronics 108 shown in FIG. 1 and FIG. 2. In certain examples, the structure wafer is processed (e.g., etched) to define the proof mass 502, the plurality of supports 506, and the one or more anchors 512. In further examples, the electric field detector 500 may also include one or more counterbalances 526 that are coupled to the proof mass 502. In certain examples, the electric field detector 500 may also include one or more sense electrodes and one or more drive electrodes, each of which are positioned on the substrate 522 and obscured in FIGS. 5A and 5B by the counterbalance 526.

In various examples, the electric field detector 500 determines one or more components of a received electric field (e.g., a biophysical signal emitted by the brain of a subject) based on measured capacitance variations due to torsional motion of the proof mass 502 in response to receiving the electric field. The proof mass 502 is supported by the plurality of supports 506, each of which form a rotationally compliant spring anchored to the substrate 522 via a respective anchor 512a, 512b. In the shown example, each support 506 is a flexured beam interposed between a side surface of the proof mass 502 and a corresponding anchor 512a, 512b. That is, a first support 506a is interposed between a first side surface of the proof mass 502 and a first anchor 512a, and a second support 506b is interposed between a second side surface of the proof mass 502 and a second anchor 512b. Each anchor is coupled to the substrate 522 with a respective anchor ground 520a, 520b. As shown in FIG. 5A, the first support 506a and the second support 506b may be coupled to opposing sides of the proof mass 502. The dimensions of the supports 506 are selected such that the overall stiffness of the respective support 506 is sufficient to withstand operational shock loads while maximizing a response to input torques. While shown as including a pair of supports 506a, 506b, in various other examples the electric field detector may include one (e.g., in a "lever" arrangement) or any number of supports 506.

In various other examples, the proof mass 502 may be levitated by an electrostatic suspension, electromagnetic suspension, and/or equivalent rotational bearing. In such an example, the levitated proof mass 502 is positioned to rotate with very low resistance and low stiffness. Such an arrangement may maximize a scale factor of the electric field detector 500 while retaining a structural stability and robustness. In such an example, the electrostatic suspension, electromagnetic suspension, and/or rotational bearing may supplement the one or more illustrated flexured beams or replace the one or more flexured beams.

Figure 9A:
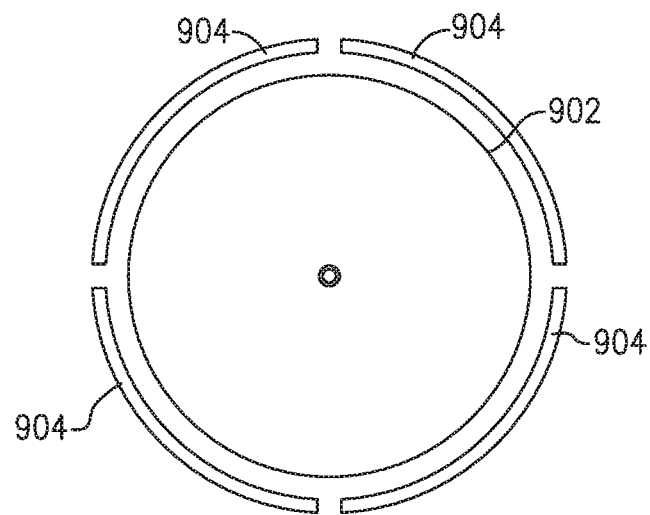
FIG. 9A is an axial view of a proof mass and levitation forcers, according to various examples discussed herein.
Figure 9B:
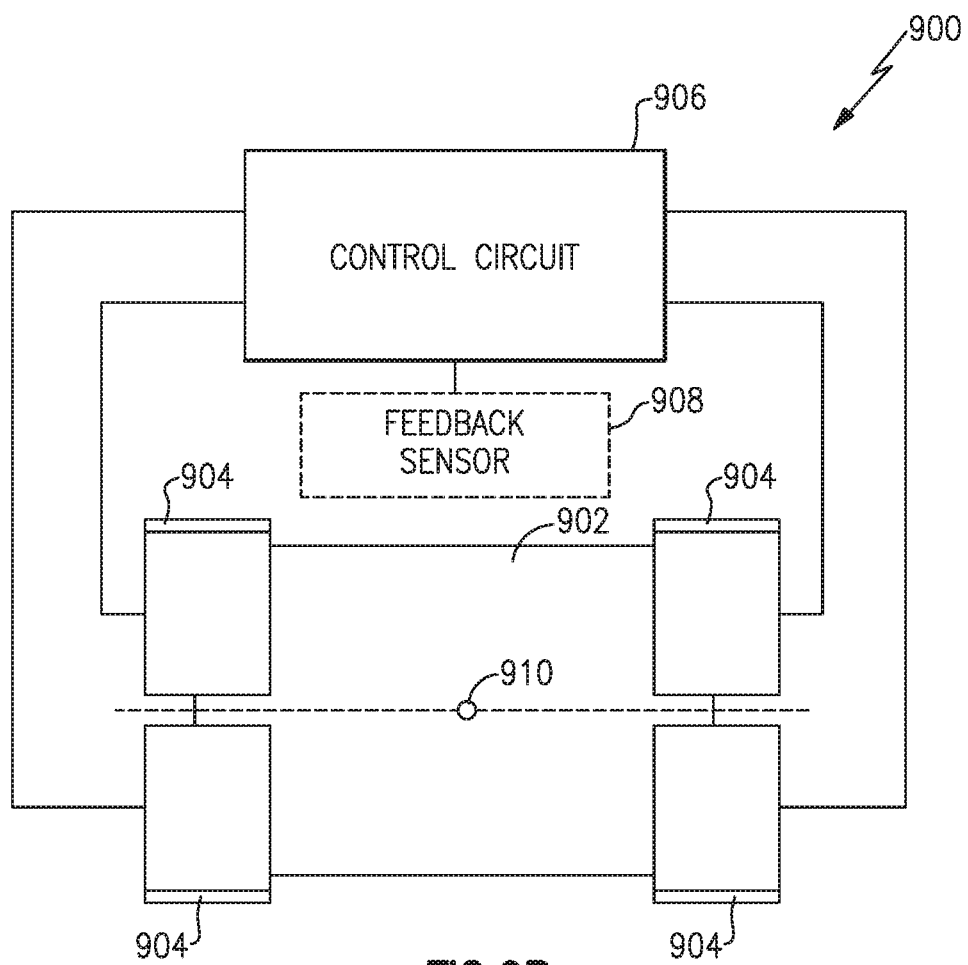
FIG. 9B is a side profile view of a levitation suspension system including the levitation forcers of FIG. 9A, according to various examples discussed herein.

One example of a levitation suspension system 900, and components thereof, are illustrated in FIG. 9A and FIG. 9B. Examples of the levitation suspension system 900 may be incorporated within any of the examples of the electric field detectors described herein, such as the electric field detector 500 described with reference to FIG. 5A and FIG. 5B. FIG. 9A illustrates an axial view of a proof mass 902 and levitation forcers 904, and FIG. 9B shows a side profile view of the levitation suspension system 900. As shown, the levitation suspension system 900 may include one or more levitation forcers 904 that apply a force to the proof mass 902 to levitate the proof mass against gravity and other induced forces. In certain examples, each of the one or more levitation forcers 904 may include one or more of the sense electrodes 702 or drive electrodes 704 further described below with reference to FIG. 7. While in certain examples, each levitation forcer 904 may be an electrostatic forcer (e.g., for electrostatic levitation), in various other examples, each levitation forcer 904 may be a magnetic forcer (e.g., for magnetic levitation).

A control circuit 906 (e.g., control circuit 800 illustrated in FIG. 8) coupled to the levitation forcers 904 receives feedback from each levitation forcer 904 and/or one or more feedback sensors 908. If a position of the proof mass 902 is displaced relative to a desired null point (e.g., shown as point 910), the control circuit 906 provides a control signal to one or more of the levitation forcers 904 to increase or decrease the force applied by the receiving levitation forcer 904 and return the proof mass 902 to the null position. In certain examples, the proof mass 902 may be metalized (e.g., at an end of the proof mass) to increase the sensitivity of the proof mass 902 to the levitation force 904. The position of the proof mass 902 (relative to the null position) may be capacitively measured based on a capacitance between the proof mass 902 and one or more sense electrodes (e.g., sense electrodes 702 described with reference to FIG. 7).

The number and arrangement of levitation forcers 904 may be selected based on the desired application of the corresponding electric field detector. While FIG. 9A illustrates a plurality of levitation forcers 904 radially aligned about the circumference of an axial proof mass 902, various other arrangements are possible. In particular, the number, shape, and arrangement of levitation forcers 904 may depend on the particular shape of the proof mass 902 and packaging constraints (e.g., size, weight, available space, etc.). In addition to maintaining the proof mass 902 a desired null position, in certain instances, the levitation forcers 904 may be used to rotate the proof mass 902 at a desired velocity, or reposition the proof mass 902 to a desired orientation. In addition to assessing the position of the proof mass 902 relative to a null position, one or more signals from the illustrated feedback sensor 908 may be used by the control circuit 906 to infer external stimuli that induce proof mass 902 movement.

Referring to FIG. 5A, in various examples, the plurality of supports 506 suspend the proof mass 502 above a substrate offset space defined in the substrate 522. That is, the substrate 522 may include an area (referred to as a "substrate offset space") formed in a surface thereof beneath the proof mass 502 (e.g., and counterbalance 526 shown in FIGS. 5A and 5B). As discussed, in certain examples, the electric field detector 500 may include one or more sense electrodes and one or more drive electrodes, each of which are positioned on the substrate 522 and in capacitive communication with the proof mass 502. In particular, each of the sense electrodes and the drive electrodes may be positioned within the substrate offset space and may form a sense gap with the proof mass 502. In certain examples, the substrate offset space is formed by etching the substrate 522; however, other processing techniques may be used, such as milling, grinding, or one or more deposition processes.

In various examples an impinging electric field concentrated on the source of concentrated charge 504 generates a torque and effects motion of the proof mass 502. For instance, the torque, τ, may be represented as:

$$\tau = p \times E$$

where, p, is the strength of the electric dipole from the source of concentrated charge 504 (e.g., in C-m) and, E, is the strength of the received electric field (e.g., in V/m).

In many instances, the proof mass 502 responds to the torque by rotating about a torque axis (shown as axis τ in FIGS. 5A and 5B). In one example, the rotation can be represented as:

$$\theta = \frac{\tau}{(Is^2) + (Ds) + k}$$

where, θ, is the angle of rotation, τ, is the torque, I, is the polar moment of inertia, s, is the complex frequency, D, is a damping coefficient, and k is the rotational stiffness. In this way, the torque generated from the electric field induces motion in the proof mass 502, which reacts against the stiffness of the supports 506.

In various examples, the rotation of the proof mass 502 increases or decreases the distance between the proof mass 502 and the sense electrodes positioned on the baseplate 514. As the distance between the proof mass 502 and the sense electrode increases or decreases, the relative capacitance between a sense electrode and the proof mass 502 varies. The resulting change in capacitance can be measured by the electronics to estimate the characteristics of the received electric field. In various examples, the electric field detector 500 may include a plurality of electrical leads 518, at least one of which couples sense electrode to a corresponding contact 516 on the baseplate 514. Each electrical contact 516 may connect the corresponding lead 518 to the control circuit, which may determine a direction, magnitude, and/or a phase of the received electric field based on the sensed variation in capacitance. As illustrated, the substrate 522 may be coupled to the baseplate 514. Accordingly, the baseplate 514 supports the substrate 522, as well as other components of the detector 500, and may include one or more fasteners for creating a seal with the cover 510.

In certain examples, the control circuit may also send one or more control signals to the electrical contacts 516 and the corresponding leads 518. In particular, the control circuit may generate one or more control signals which can be used to charge a drive electrode and produce a feedback torque on the proof mass 502. That is, the electric field detector 500 may further include one or more drive electrodes positioned on the substrate 522 (e.g., within the substrate offset space) which rebalance the proof mass 502 to a nominal rotational position based on a received control signal. Such an arrangement may reduce non-linearities in the capacitance measurements (e.g., from the supports 506) while also extending the dynamic range of the electric field detector 500. In such an example, a lead 518 may receive the control signal from a contact 516 and provide the control signal to a drive electrode.

In certain examples, the electric field detector 500 may include a source of concentrated charge 504 (e.g., concentrated electrical charge). In the example shown in FIG. 5A, the source of concentrated charge 504 is coupled to a top surface of the proof mass 502; however, in certain other examples, the proof mass 502 itself may be composed of charge concentrated material. That is, a body of the proof mass 502 may be composed of a source of concentrated charge. In various examples, the source of concentrated charge 504 may include any suitable source of a semi-permanent static electric dipole, such as an electret or a capacitor plate having a residual free charge and/or polarization. As will be understood to one of ordinary skill in the art, the term "electret" refers to the dielectric equivalent of a permanent magnet.

For example, an electret configured for use in the detector 500 may be formed by: (a) applying heat to the electret material, (b) in response to obtaining a predetermined temperature, applying a voltage to the electret material, at which point the electret material will act like a capacitor and store the applied charge, and (c) cooling the electret material to a predetermined temperature. Thereafter, the electret maintains a residual charge after the field is removed. As an additional example, the electret material may be bombarded with radiation to generate a residual charge. Accordingly, real surface charges or aligned dipoles are immobilized in the bulk of the dielectric material.

Materials such as Polytetrafluoroethylene (PTFE), silicon nitride, Fluorinated Ethylene Propylene (FEP), a Perfluoroalkoxy alkane (PFA) material, Cyptop, Cylotene, and other dielectrics may be suitable materials that can be used as an electret. In certain examples the electret may include, but is not limited to, Thermo-electrets, MPEs (metal-polymer electrets), Radio-electrets, and Mechanoelectrets. In some examples, the source of concentrated charge 504 may be charged (i.e., applied a voltage) prior to coupling the source of concentrated charge 504 to the proof mass 502. In certain other examples, the source of concentrated charge 504 may be first coupled to the proof mass 502, and then charged. After formation, residual surface potentials can be maintained with no power input since the charge is retained in the source of concentrated charge 504 (e.g., in deep traps within the electret material). In some instances, the residual surface potential may be more than 1 kV.

Further examples may include a series of two or more stacked electrets or a plurality of electrets arranged in a predetermined order. To increase the strength of the electric dipole, and therefore increase the sensitivity of the detector 500 to electric fields, micron-thick layers of electrets may be stacked together. Metal layers may be interposed between one or more layers of the source of concentrated charge 504 (e.g., stacked electret layers) to increase the gain of the one of more field concentrators 508 positioned adjacent the proof mass 502. For example, the metal layers of some embodiments may include layers of gold or platinum.

In other examples, the source of concentrated charge 504 may generate a semi-permanent dynamic electric dipole by driving a piezo-electric material (e.g., PZT). For instance, the control circuit may continuously, or periodically, drive the PZT to refresh the charge distribution when depleted. In other examples, the control circuit may actively generate a voltage gradient across the proof mass 502 of the electric field detector 500 to generate a dynamic electric dipole. In such an example, one or more electrodes or Piezo-electric materials may supply an induced voltage (e.g., active excitation signal) to vary a dynamic electric dipole at the proof mass 502. Specifically, the electrodes may be driven by the control circuit at an alternating-current (AC) frequency such that the detector 500 up-converts (e.g., increases a frequency) the received electric field information to a frequency above a 1/f noise limit, improving the performance of the detector 500.

As illustrated in at least FIGS. 5A-5B, in at least one example the proof mass 500, the supports 506, and the anchors 512a, 512b are defined in the same structure wafer. For instance, the substrate may include a Silicon-on-Insulator wafer having a flexure layer, a handle layer, and an interposed oxide layer. The proof mass 502, supports 506, and anchors 512a, 512b may be defined in the flexure layer. It is appreciated that in some instances, the source of the concentrated charge 504 and/or an intervening material (e.g., a glue or other adhesive material) between the source of concentrated charge 504 and the proof mass 502 may introduce an asymmetry in a balance of the proof mass 502. Such an asymmetry may generate undesired sensitivities to external accelerations. In one example, the electric field detector 500 may compensate for the external accelerations by directly measuring the external acceleration with an auxiliary sensor, and adjusting the measured electric field to compensate for the accelerations. In certain examples, the electric field detector 500 may include the one or more counterbalances 526 to compensate for the asymmetry.

Figure 6:
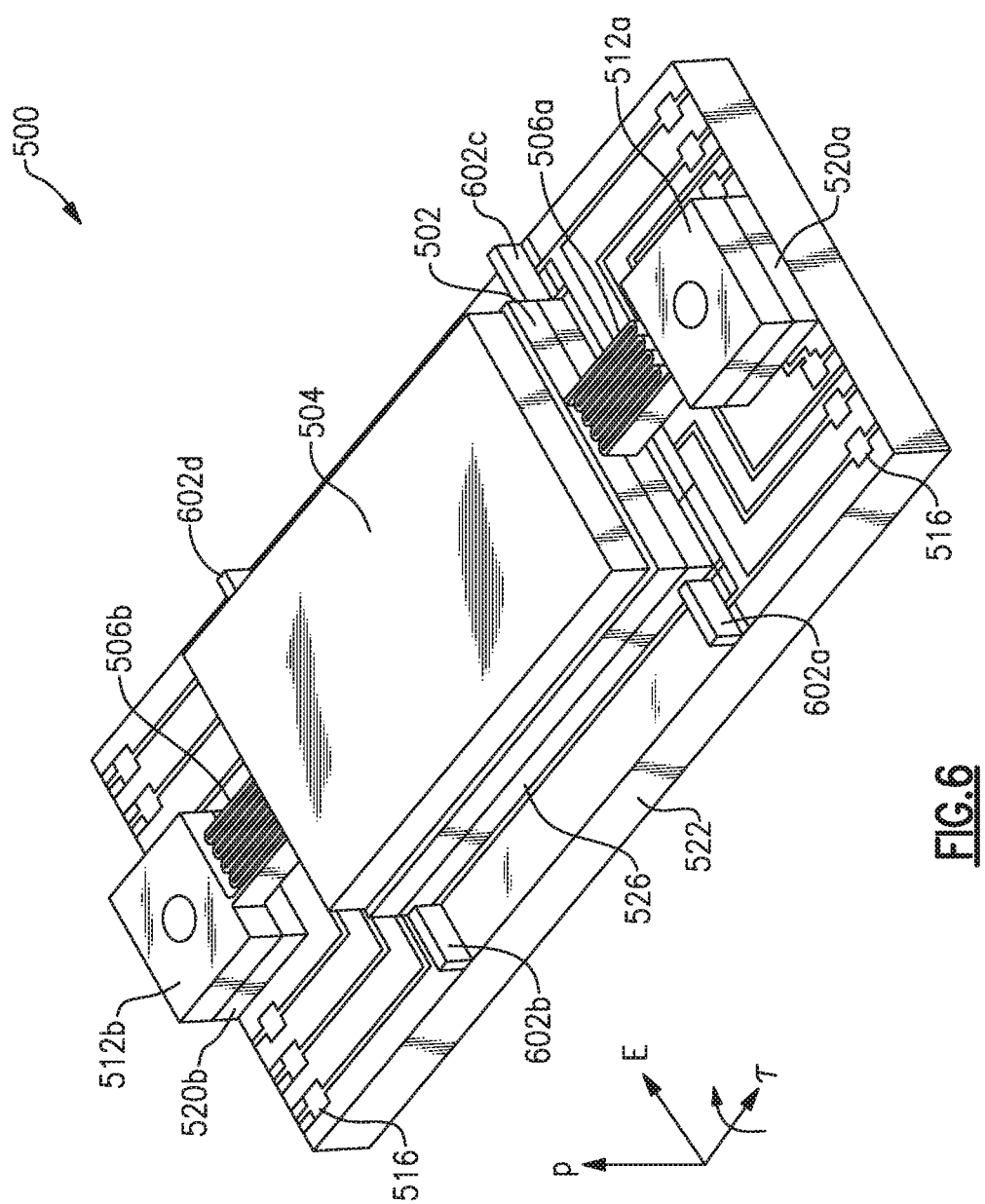
FIG. 6 is another perspective view of the electric field detector illustrated in FIG. 5A, according to examples discussed herein.

Referring to FIG. 6, there is illustrated a view of the electric field detector 500 shown in FIGS. 5A and 5B having the cover 510 and the baseplate 514 removed. In FIG. 6, a counterbalance 526 is positioned on a bottom surface of the proof mass 502 and suspended above the substrate offset space. The counterbalance 526 reduces the pedulosity of the proof mass 502 and, therefore, a sensitivity of the proof mass 502 to undesired inputs, such as vibrations. In further examples, mechanical stops 602a-d may be coupled to the counterbalance 526 to prevent large excursions of the proof mass 502 from a predefined area of travel. That is, the mechanical stops 602a-d may be positioned to define a limit of travel of the proof mass 502. For example, FIG. 6 shows a first, second, third, and fourth mechanical stop 602a, 602b, 602c, 602d coupled to a side surface of the counterbalance 526.

Returning to FIGS. 5A and 5B, the flux concentrators 508 can operate to focus the received electric field on the source of concentrated charge 504. As shown, the flux concentrators 508 may be integrated within the cover 510, and in particular, attached to an interior surface of the cover 510. In various examples, the flux concentrators 508 magnify the intensity of the electric field near the location where the electric field intercepts the source of concentrated charge 504. The flux concentrators 508 may each be composed of metal, or a material with a high dielectric constant, which routes the flux through a spatial volume thereof. For example, each flux concentrator 508 may be composed of copper. By positioning the flux concentrators 508 near the source of concentrated charge 504, the electric field is concentrated to provide a gain at the source of concentrated charge 504. In the shown example, a first flux concentrator 508a is positioned proximate a third side surface of the proof mass 502 and a second flux concentrator 508b is positioned proximate a fourth surface of the proof mass 502.

In various examples, each flux concentrator 508 is positioned as close as possible to the source of concentrated charge 504 to maximize the provided gain. The performance of each flux concentrator 508 may also be enhanced by increasing a length and/or an area of the respective concentrator 508 to maximize the amount of flux received and directed to the source of concentrated charge 504. Relative to the cover 510, each flux concentrator 508 may be internal, external, or a combination of both depending upon the level of enhancement desired. In addition to the flux concentrators 508, in certain examples the electric field detector 500 may include additional signal processing components which enhance the ability of the electric field detector 500 to resolve small signals. Such components are further described below with reference to at least FIG. 8. According to certain other examples, the one or more sense electrodes and the one or more drive electrodes that provide the capacitive readout may be replaced by other structures that are configured to measure the torque on the proof mass 502 from a received electric field. For instance, the electric field detector 500 may include one or more sensors that measure the torque by its effect on a frequency of one or more of the plurality of supports 506, or one or more sensors that optically measure a displacement of the proof mass 502.

As also shown in FIGS. 5A and 5B, in various examples the electric field detector 500 includes the cover 510. The cover 510 is positioned to encompass the other components of the electric field detector 500, such as the proof mass 502, the plurality of supports 506, the one or more flux concentrators 508, the one or more anchors 512, the substrate 522, the sense electrodes, the drive electrodes, and the one or more electrical contacts 516, among other components. In certain examples, the cover 510 may provide a vacuum environment which reduces the sensitivity of the electric field detector 500 to acoustic coupling and air damping, which reduces Brownian noise. A vacuum environment also helps to ensure that a minimal charge is maintained by preventing the dielectric breakdown of air within the electric field detector 500. In addition to these benefits, the cover 510 protects the discussed components of the electric field detector 500 from dust, moisture, and other contaminants. In one example the cover 510 may be formed from transparent glass to permit displacement of the proof mass 502 to be measured optically.

According to an example, a scale factor of the electric field detector 500 may be increased by using one or more bias voltages to create an electrostatic spring with a negative stiffness relative to the mechanical stiffness of the supports 506. A strong bias voltage on a sense electrode, drive electrode, and/or other nearby electrodes generates a force which is opposite of the mechanical spring force of the supports 506, and thereby decreases the overall stiffness of the structure. Accordingly, when summed, the negative stiffness reduces the total stiffness of the electric field detector 500 and increases the response of the proof mass 502 to a received electric field. Such an approach provides the benefit of increased performance without the loss of robustness, which would otherwise result if the stiffness of each of support 506 was mechanically reduced. While in certain examples the electric field detector 500 may include additional electronics to create a negative spring by force inputs (e.g., a control loop or a magnetic field), application of bias voltages to create an electrostatic spring provides the benefit of low-noise performance and reduced complexity.

Figure 7:
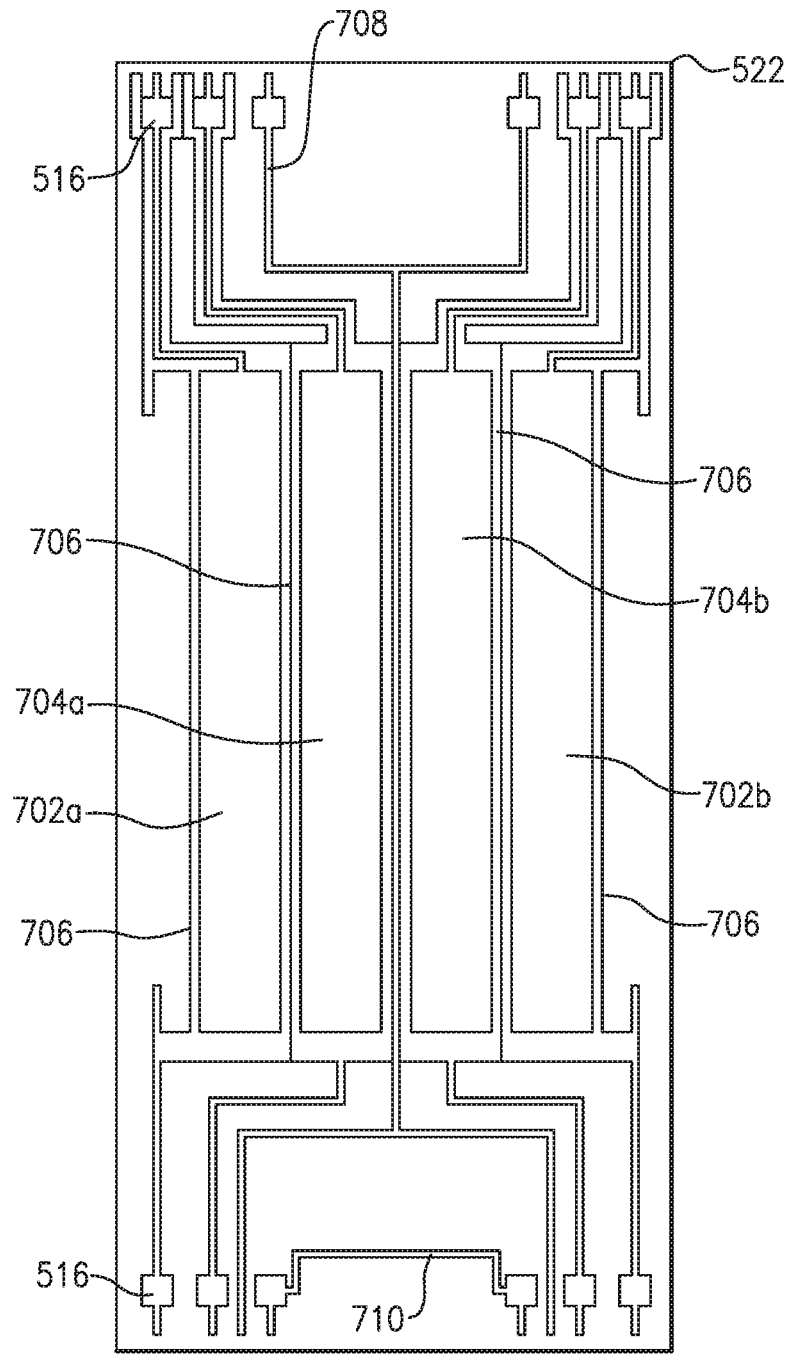
FIG. 7 is a plan view of the sense electrodes and drive electrodes of the electric field detector illustrated in FIG. 5A, according to examples discussed herein.

Referring now to FIG. 7, illustrated is a plan view of the sense electrodes 702a, 702b (collectively "sense electrodes 702") and drive electrodes 704a, 704b (collectively "sense electrodes 704") of the electric field detector 500 illustrated in FIGS. 5A and 5B. In particular, FIG. 7 illustrates the electrical connections between the sense electrodes 702 and the corresponding electrical contacts 516, and the electrical connections between the drive electrodes 704 and the corresponding electrical contacts 516. For the convenience of illustration, leads 518 are not shown in FIG. 7. As discussed above with reference to FIGS. 5A and 5B, in various examples the sense electrodes 702 and the drive electrodes 704 are formed on the substrate 522, and in particular, within the substrate offset space beneath the proof mass 502. FIG. 7 is described with continuing reference to the electric field detector 500 illustrated in FIGS. 5A and 5B, and the components thereof.

FIG. 7 illustrates a first sense electrode 702a (e.g., a left sense electrode), a second sense electrode 702b (e.g., a right sense electrode), a first drive electrode 704a (e.g., a left torquer), and a second drive electrode 704b (e.g., a right torquer). Each of the first sense electrode 702a, second sense electrode 702b, first drive electrode 704a, second drive electrode 704b, and electrical contacts 516 may be applied as a metallization layer to the substrate 522. For instance, each sense electrode 702, each drive electrode 704, and/or each electrical contact 516 may be a layer of chrome, platinum, or gold.

In one example, the two sense electrodes 702a, 702b are used for a differential capacitance measurement and the two drive electrodes 704a, 704b are used as torquers for force feedback during closed loop operation. Each sense electrode 702 and drive electrode 704 is interposed between a pair of respective electrical contacts 516 and extended along a length of the substrate 522. While shown in FIG. 7 as a pair of sense electrodes 702 and a pair of drive electrodes 704, each plate having a substantially rectangular shape, in various other examples any suitable number of sense electrodes 702 and drive electrode 704 may be used, and each sense electrode 702 or drive electrode 704 may have any suitable shape. Moreover, in certain examples the first sense electrode 702a and the first drive electrode 704a may be connected and act as a single large electrode to maximize performance when not operating in a closed loop mode of operation. In such an example, the second sense electrode 702b and the second drive electrode 704b may be coupled in a similar manner. In certain examples, the sense electrodes 702 and the drive electrode 704 may be reversed and their relative areas chosen to optimize the relative level of performance between the drive and sense operations. In one example, the sense electrodes 702a, 702b (e.g., the outer positioned electrodes) act on the plurality of supports 506 of the detector 500, and therefore may have a greater effectiveness.

In various examples, each sense electrode 702 and drive electrode 704 may include a respective guard ring 706. As shown, the proof mass 502 may also have a guard ring 708. Each guard ring 706 substantially surrounds the respective sense electrode 702 or drive electrode 704 and separates that sense electrode 702 or drive electrode 704 from the other sense electrode 702 and drive electrode 704. In one example, each the guard ring 706 is a thin metal track that traces the perimeter of the corresponding plate or electrode. Each guard ring 706, 708 substantially eliminates direct-current (DC) current and low-frequency leakage currents from unintentionally effecting the corresponding sense electrode 702, drive electrode 704, or proof mass 502. DC current and low-frequency leakage current may limit the dynamic range of the electric field detector 500 and may create low-frequency noise by producing undesired voltages in the source impedances. FIG. 7 further shows a ground contact 710 for the proof mass 502.

Figure 8:
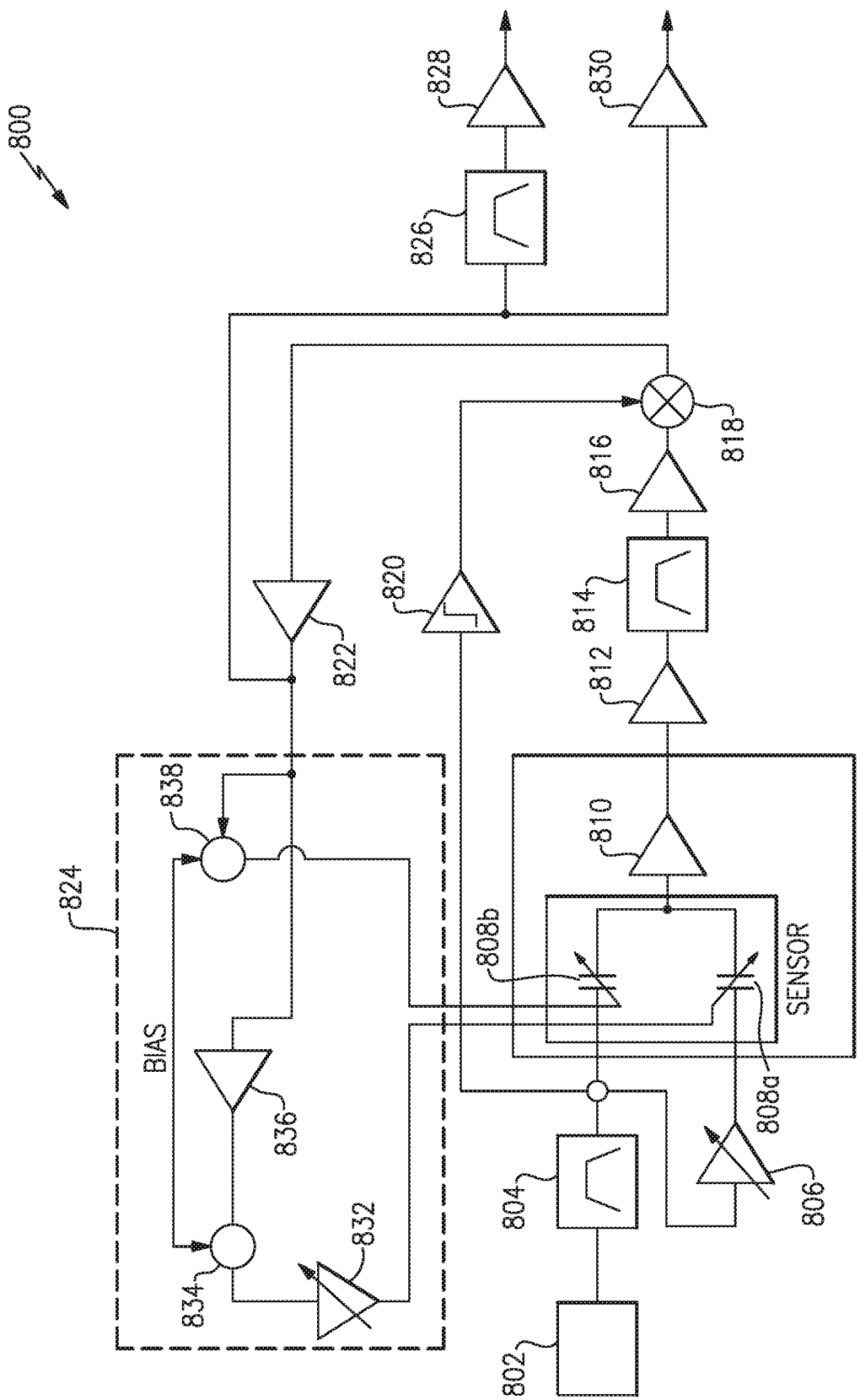
FIG. 8 is a block diagram of a control circuit according to examples discussed herein.

Turning now to FIG. 8, shown is one example of a control circuit 800 that may be coupled to the electric field detector 500 illustrated in FIGS. 5A and 5B to detect the components of an electric field received at the detector 500 and/or provide one or more control signals. For example, the control circuit 800 may be incorporated within the control system 202 illustrated in FIG. 2. In other examples, the control circuit 800 may be integrated within the control electronics 108 shown in FIGS. 1 and 2, or split and integrated within a combination of the control system 202 and the control electronics 108. In various examples, the control circuit 800 may be coupled to the contacts 516 illustrated in FIGS. 5A and 5B. FIG. 8 is discussed with continuing reference to the electric field detector 500 of FIGS. 5A and 5B, and the components thereof.

In certain examples, the control circuit 800 may include any processing component or controller (e.g., processing component 210 in FIG. 2). The processing component may be connected to a memory and a data storage element (e.g., memory 206 and data storage 222 shown in FIG. 2). The memory stores a sequence of instructions coded to be executable by the processing component to perform or instruct the various components discussed herein to perform the various processes and acts described in this disclosure. For instance, the control circuit 800 may communicate with, and provide one or more control signals to the sense electrodes and the drive electrodes of the electric filed detector via the contacts 516 and the leads 518.

In the illustrated example, the control circuit 800 includes a precision square-wave generator 802 which is coupled to a first filter 804. The precision square-wave generator 802 generates a signal which is converted to a sine wave by the first filter 804. The first filter 804 may include any suitable filter designed to accept a square-wave input and provide a sinusoidal output. For instance, one example is a low-Q active bandpass filter with a notch filter to reduce the third-order harmonic. In various examples, the first filter 804 has a very low amplitude sensitivity to temperature, such as 1-3 ppm per degree Celsius. The first filter 804 is coupled to an inverting amplifier 806 which has an adjustable gain and a nominal gain of −1. Accordingly, an output of the first filter 804 and the inverting amplifier 806 form a low-noise differential sine-wave carrier generator.

As shown in FIG. 8, the carrier generator may be coupled to each of the sense electrodes (e.g., shown as readout capacitors 808a, 808b, collectively "readout capacitors" 808) to excite the readout capacitors 808 in order to up-convert (e.g., increase a frequency) an electronics signal produced by the received electric field. In various examples, by up-converting the received electric field information, the information converted to a frequency where amplifier noise is significantly lower. Moreover, the up-conversion reduces the sensitivity of the electric field to current noise sources in a preamplifier 810 coupled to the readout capacitors 808. While not illustrated in FIG. 8, in many instances the control circuit 800 may include one or more passive high-pass filters interposed between the outputs of the carrier generator and the readout capacitors 808 to reduce low-frequency voltage noise coupled to the readout capacitors 808 from the carrier generator. Such an arrangement offers the benefit of reduced low-frequency torque noise.

Referring to the electric field detector 500 of FIG. 5A, in the absence of an electric field, there will be no torque on the proof mass 502 (in an ideal case). In such a situation, no electric field information is passed from the readout capacitors 808 (sense electrodes in FIG. 7) to the preamplifier 810. However, when an electric field is present, the readout capacitors 808 provide a measured signal to the preamplifier 810, which in turn provides an output of a carrier signal amplitude-modulated by the electric field (e.g., a double-sideband suppressed carrier signal).

In various examples, the control circuit 800 includes a second amplifier 812 and a second filter 814 coupled to the output of the preamplifier 810. For instance, the second amplifier 812 may include a low-noise instrumentation amplifier with an input-referred noise density that is substantially less than the output-referred noise density. The carrier signal amplitude-modulated by the electric field is received and amplified by the second amplifier 812 before being filtered by the second filter 814. According to certain examples, the second filter 814 includes a bandpass filter which has a low quality factor to reduce the noise within amplitude-modulated carrier signal at the third order and higher order harmonics. Accordingly, the second filter 814 provides filtering functionality to prevent higher order harmonics from affecting the noise performance of the control circuit 800 after the carrier signal has been demodulated. In certain implementations, the control circuit 800 may also include a third amplifier 816 which is coupled to an output of the second filter 814 and configured to add an additional gain to the carrier signal amplitude-modulated by the electric field information. While illustrated in FIG. 8 as separated from the second filter 814, in certain examples the third amplifier 816 provides additional AC gain and may be incorporated into the second filter 814.

As shown in FIG. 8, the control circuit 800 includes a demodulator 818 and comparator 820 which are coupled to form a switching (or square-wave) demodulator. In FIG. 8, the switching demodulator is coupled to an output of the third amplifier 816. The demodulator 818 drives a controller 822, which is coupled to the output of the demodulator 818. In some examples, the controller 822 may include an Integral-Derivative (ID) controller, a Proportional-Integral-Derivative (PID) controller, or any other suitable predictive controller. In one example, the controller 822 drives a torque generator 824 which produces a bias voltage at each respective torque generator electrode (e.g., drive electrodes 704a, 704b illustrated in FIG. 7). In particular, the torque generator may produce respective torque generator voltages of (BIAS+K*$V_C$) and (BIAS−K*$V_C$), where "BIAS" is a bias voltage, "K" is a scaling constant, and "$V_C$" is the output of the controller 822. For example, the torque generator 824 may produce a substantially constant bias voltage having a nominal value near one-half of the positive or negative supply voltage. While in the illustrated example, the torque generator 824 includes summation blocks 834, 838, an inverting gain 836, and an adjustable gain 832 for the purpose of illustration, in various other examples the torque generator 824 may be implemented with various other suitable components.

Accordingly, the applied torque, which is proportional to the square of the voltage, is directly proportional to the output of the controller 822. Such a biasing arrangement achieves a linearization of the closed-loop feedback torque applied to the proof mass 502 with respect to the output of the controller 822. This arrangement results in a linear control loop and permits a linear readout of the electric field information. In certain examples, the control circuit 800 may further include one or more passive low-pass filters (not shown) interposed between the torque generator 824 and the torque generator electrodes in order to reduce carrier-band noise applied to the torque generator electrodes.

As further illustrated in FIG. 8, the control circuit 800 may include a baseband filter 826 coupled to the output of the controller 822. For example, the baseband filter 826 may include a bandpass filter having a passband selected to extract the electric field information within the desired bandwidth from the output of the demodulator 818. The output of the baseband filter 826 may then be amplified by a fourth amplifier 828 and provided to an output of the control circuit 800 or one or more downstream diagnostic electronics. In at least one example, the fourth amplifier 828 is designed such that most of a variable voltage range of the amplifier 828 corresponds to a maximum expected in-band field strength of the electric field. Such a design provides the benefit of reduced noise. For instance, the fourth amplifier 828 may include a high-gain amplifier that has a gain of about 100. The parameters of the fourth amplifier 828 may be selected in conjunction with the parameters of the baseband filter 826 to select and amplify a desired frequency band (e.g., a frequency band associated with brain activity (0.5 Hz-100 Hz)). As shown, in certain examples the control circuit 800 may also include a fifth amplifier 830 to provide an unfiltered output for diagnostic purposes.

Though the features within FIG. 8 are illustrated as blocks within a block diagram, unless otherwise indicated, the features may be implemented as one of, or a combination of, analog circuitry, digital circuitry, or one or more microprocessors executing software instructions. For example, software instructions may include digital signal processing (DSP) instructions to be executed by a digital signal processor.

While FIGS. 5A-7 offer some examples of possible arrangements of a contactless electric field detector configured to sense an electric field component of an electromagnetic signal, in other examples, various other arrangements may be used. For instance, instead of being capacitively sensed, in various other examples the contactless electric field detectors described herein may be coupled to one or more mechanical supports each having a resonant frequency that can be measured to determine the torque and strength of the electric field. In other examples, an optical sensor may be positioned to direct an optical beam at a proof mass of an electric field detector. Motion of the proof mass causes deflection of the optical beam, which can be directly or indirectly measured to determine the component of the electric field. Various other techniques may be used and are within the scope of this disclosure.

Figure 10:
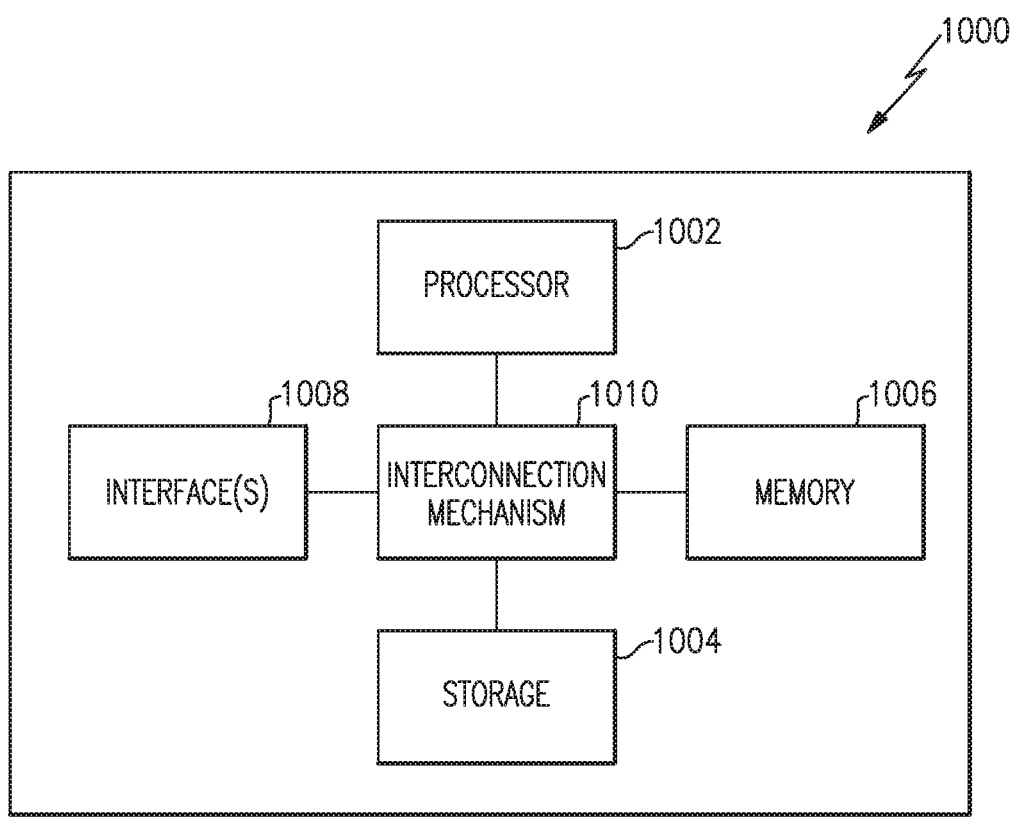
FIG. 10 is a functional block diagram of an example of a computing system configured to implement various examples of the processes described herein.

Referring to FIG. 10, illustrated is one example of a control system (e.g., a computing device or controller 1000) that may implement software routines corresponding to the processes described above with reference to at least FIG. 1 and FIG. 2. The controller 1000 may include a processor 1002, a data storage 1004, a memory 1006, and one or more interfaces 1008, such as a system interface and/or a user interface. While not explicitly illustrated in FIG. 10, in certain examples the controller 1000 may be coupled to a power source. The power source may deliver power to one or more components of the controller 1000, as well as other components of the sensing assembly 100, sensing system 200, and feedback system 204.

In FIG. 10, the processor 1002 is coupled to the data storage 1004, memory 1006, and the various interfaces 1008. The memory 1006 stores data and/or sequences of instructions coded to be executable by the processor 1002 during operation of the controller 1000. Thus, the memory 1006 may be a relatively high performance, volatile, random access memory such as a dynamic random access memory ("DRAM") or static memory ("SRAM"). However, the memory 1006 may include any device for storing data, such as a disk drive or other nonvolatile storage device. Various examples may organize the memory 1006 into particularized and, in some cases, unique structures to perform the functions disclosed herein. These data structures may be sized and organized to store values for particular data and types of data.

The data storage 1004 includes a computer readable and writeable data storage medium configured to store non-transitory instructions and other data, and can include non-volatile storage media, such as optical or magnetic disk, ROM or flash memory. The instructions may include executable programs or other code that can be executed by the at least one processor 1002 to perform any of the functions described herein.

In various examples, the controller 1000 includes several interface components 1008, such as a system interface and/or a user interface. Each of the interface components 1008 is configured to exchange, e.g., send or receive, data with other components of the controller 1000 (and/or associated transmitter or receiver), or other devices in communication with the controller 1000. According to various examples, the interface components 1008 may include hardware components, software components, or a combination of hardware and software components. In certain examples, components of the system interface couples the processor 1002 to one or more other components of the sensing system shown in FIG. 1. The system interface may provide one or more control signals to any such components and may manage the operation of such components, as described above.

A user interface may include hardware and/or software components that allow the controller 1000 to communicate with an external entity, such as a user. These components may be configured to receive information from user interactions with the user interface. Examples of the components that may be employed within the user interface include buttons, switches, light-emitting diodes, touch screens, displays, stored audio signals, voice recognition, or an application on a computer-enabled device in communication with the controller 1000. Data received at the various interfaces may be provided to the processor 1002, as illustrated in FIG. 10. Communication coupling (e.g., shown interconnection mechanism 1010) between the processor 1002, memory 1006, data storage 1004, and interface(s) 1008 may be implemented as one or more physical busses in conformance with standard, proprietary, or specialized computing bus technologies.

The processor 1002 performs a series of instructions that result in manipulated data that is stored in and retrieved from the data storage 1004, as discussed above. In various examples, the series of instructions result in interpretation of the sensor data discussed herein. Such instructions may correspond to commands for correcting sensor data, estimating an electric field based on sensor data, and providing one or more control signals to operate a feedback system, as also discussed herein.

The processor 1002 may be any type of processor, multiprocessor or controller, whether commercially available or specially manufactured. For instance, the processor may include a commercially available processor, such as a processor manufactured by INTEL, AMD, MOTOROLA, or FREESCALE. In some examples, the processor 1002 may be configured to execute an operating system, such as a real-time operating system (RTOS), for instance RTLinux, or a non-real time operating system, such as BSD or GNU/Linux. The operating system may provide platform services to application software. These platform services may include inter-process and network communication, file system management and standard database manipulation. One or more of many operating systems may be used, and examples are not limited to any particular operating system or operating system characteristic.

Having thus described several aspects of at least one embodiment, it is to be appreciated various alterations, modifications, and improvements will readily occur to those skilled in the art. Such alterations, modifications, and improvements are intended to be part of this disclosure and are intended to be within the scope of the disclosure. Accordingly, the foregoing description and drawings are by way of example only.

What is claimed is:

1. A biophysical sensing system comprising:
 a sensing assembly including an array of contactless electric field detectors, each of the contactless electric field detectors being a microelectromechanical system (MEMS) electric field detector including at least a proof mass configured to sense a corresponding vector component of an electric field generated by a body of a subject based on a displacement of the proof mass;

a control system coupled to the sensing assembly to receive sensor data indicative of the vector components of the electric field sensed by each of the contactless electric field detectors, the control system being configured to generate an estimate of the electric field based at least in part on the sensor data; and a feedback system coupled to at least the control system, the feedback system including at least one feedback interface, the feedback system being configured to operate the feedback interface to provide feedback to the subject based on the estimate of the electric field.

2. The biophysical sensing system of claim 1, wherein the feedback interface is at least one of a visual display, a speaker, a haptic transducer, a heating or cooling source, and a chemical source.

3. The biophysical sensing system of claim 2, wherein the feedback system includes a housing configured to attach to the subject, the at least one of the visual display, the speaker, the haptic transducer, the heating or cooling source, and the chemical source being coupled to the housing.

4. The biophysical sensing system of claim 3, wherein the feedback is at least one of a series of visual images from the visual display, an auditory feedback from the speaker, a vibration or pressure sensation from the haptic transducer, a heat stimuli or a cooling stimuli from the heating or cooling source, and a chemical stimulus from the chemical source.

5. The biophysical sensing system of claim 1, wherein the control system is configured to compare the estimate of the electric field to an electric field template of a mental state, and instruct the feedback system to operate the feedback interface to induce a neural response in the subject based on a difference between the estimate of the electric field and the electric field template of the mental state.

6. The biophysical sensing system of claim 5, wherein the neural response includes one or more neural oscillations, the feedback system being configured operate the feedback interface to suppress or augment the one or more neural oscillations.

7. The biophysical sensing system of claim 5, wherein the neural response includes an evoked potential, the feedback system being configured operate the feedback interface to modify the evoked potential.

8. The biophysical sensing system of claim 1, wherein the control system is configured to compare the estimate of the electric field to an electric field template of a mental state, and the feedback system is configured to operate feedback interface to match a subsequent estimate of the electric field to the electric field template of the mental state.

9. The biophysical sensing system of claim 1, wherein the feedback interface includes at least one active stimulator, the feedback system being configured to operate the active stimulator to provide a stimulus to the subject based at least in part on the estimate of the electric field.

10. The biophysical sensing system of claim 1, wherein the control system is further configured to generate an input for a human-machine interface based at least in part on the estimate of the electric field.

11. The biophysical sensing system of claim 1, wherein the contactless electric field detectors are positioned to measure electrical activity of the subject's heart.

12. A biophysical sensing assembly comprising:

an array of contactless electric field detectors, each of the contactless electric field detectors being a microelectromechanical system (MEMS) electric field detector including at least a proof mass, each of contactless electric field detectors being configured to sense a corresponding component of an electric field generated by a body of a subject based on a displacement of the proof mass;

control electronics electrically coupled to each of the contactless electric field detectors, the control electronics configured to provide sensor data based on the corresponding components of the electric field;

an electromagnetic shield interposed between the array of contactless electric field detectors and the control electronics, the electromagnetic shield being positioned to electromagnetically isolate at least the array of contactless electric field detectors from electromagnetic interference from the control electronics; and a housing positioned to enclose at least the array of contactless electric field detectors, the control electronics, and the electromagnetic shield, and to suspend the array of contactless electric field detectors relative to the subject.

13. The biophysical sensing assembly of claim 12, wherein the housing is a headpiece.

14. The biophysical sensing assembly of claim 13, wherein the electromagnetic shield is a Faraday cage.

15. The biophysical sensing assembly of claim 12, wherein the control electronics include at least one auxiliary sensor positioned proximate at least one contactless electric field detector of the array of contactless electric field detectors to detect a source of noise in the sensor data.

16. The biophysical sensing assembly of claim 15, wherein the auxiliary sensor includes at least one of an additional electric field detector positioned to sense an external electric field, an inertial sensor positioned to sense movement of the subject, and a physiological sensor to sense a physiological characteristic of the subject.

17. The biophysical sensing assembly of claim 12, wherein the contactless electric field detectors are positioned to measure electrical activity of the subject's heart.

18. A biophysical feedback method, the method comprising:

sensing components of an electric field generated by a body of a subject at each of an array of contactless electric field detectors positioned proximate the subject;

receiving sensor data from the array of contactless electric field detectors at a control system, the sensor data indicative of the components of the electric field sensed by each of the contactless electric field detectors of the array of contactless electric field detectors;

generating, at the control system, an estimate of the electric field based at least in part on the sensor data;

comparing the estimate of the electric field to an electric field template of a mental state;

operating at least one feedback interface of a feedback system to provide feedback to the subject based on the estimate of the electric field; and controlling the feedback interface to induce a neural response in the subject based on a difference between the estimate of the electric field and the electric field template of the mental state.

19. The biophysical feedback method of claim 18, further comprising controlling the feedback interface to match a subsequent estimate of the electric field to the electric field template of the mental state.

20. The biophysical feedback method of claim 18, wherein the neural response includes one or more neural oscillations, and operating the at least one feedback interface includes at least one of displaying a series of visual images on a visual display, radiating auditory feedback from a speaker, generating a vibration or pressure sensation from a haptic transducer, generating a heat stimuli or a cooling stimuli from a heating or cooling source, and providing a chemical stimulus from a chemical source, to suppress or augment the one or more neural oscillations.

21. The biophysical feedback method of claim 18, wherein the neural response includes an evoked potential, and operating the at least one feedback interface includes displaying a series of visual images on a visual display, radiating auditory feedback from a speaker, generating a vibration or pressure sensation from a haptic transducer, generating a heat stimuli or a cooling stimuli from a heating or cooling source, and providing a chemical stimulus from a chemical source, to modify the evoked potential.

22. The biophysical feedback method of claim 18, further comprising generating an input for a human-machine interface based at least in part on the estimate of the electric field.

\* \* \* \* \*